US007105557B2

(12) United States Patent
Rukhman et al.

(10) Patent No.: US 7,105,557 B2
(45) Date of Patent: Sep. 12, 2006

(54) POLYMORPHS OF VALSARTAN

(75) Inventors: Igor Rukhman, Technion (IL); Evgeni Flyaks, Kiriat-Bialik (IL); Tamas Koltai, Petah Tiqva (IL); Judith Aronhime, Rehovot (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 11/140,148

(22) Filed: May 27, 2005

(65) Prior Publication Data

US 2005/0222233 A1   Oct. 6, 2005

Related U.S. Application Data

(62) Division of application No. 10/802,627, filed on Mar. 17, 2004.

(60) Provisional application No. 60/473,640, filed on May 28, 2003, provisional application No. 60/455,286, filed on Mar. 17, 2003.

(51) Int. Cl.
  *A61K 31/41*  (2006.01)
  *C07D 261/04* (2006.01)
(52) U.S. Cl. ...................... 514/381; 548/253
(58) Field of Classification Search ........... 514/381; 548/253
  See application file for complete search history.

(56) References Cited

U.S. PATENT DOCUMENTS 5,260,325 A    11/1993   Markwalder et al.
5,399,578 A *  3/1995    Buhlmayer et al. ......... 514/381
5,965,592 A    10/1999   Buhlmayer et al.
6,271,375 B1   8/2001    Villa et al.
6,294,197 B1   9/2001    Wagner et al.
6,395,728 B1   5/2002    Webb et al.
6,465,502 B1   10/2002   Bullock et al.
6,485,745 B1   11/2002   Wagner et al.

FOREIGN PATENT DOCUMENTS

EP   0 443 983      8/1991
WO   WO97/30036    8/1997
WO   WO99/67231    12/1999
WO   WO 01/82858   11/2001
WO   WO 02/06253   1/2002
WO   WO 03/070246  8/2003
WO   WO 03/089417  10/2003
WO   WO 04/026847  4/2004

OTHER PUBLICATIONS

Peter Buhlmayer, et al., Bioorgan. & Med. Chem. Let., 4(1) 29-34 (1994).
Th. Moenius, et al., J. Labelled Cpd. Radiopharm., 43(13) 1245-1252 (2000).
Borka L., et al., "Crystal Polymorphism of Pharmaceuticals", Acta Pharm. Jugosl., 40, (1990) 71-94.
Merck Index (12th edition, p. 1691, Valsartan n. 10051).
Qingzhong Jia, et al., Zhongguo Yiyao Gongye Zazhi, 32(9) 385-387 (2001).

* cited by examiner

*Primary Examiner*—Kamal A. Saeed
*Assistant Examiner*—Susannah L. Chung
(74) *Attorney, Agent, or Firm*—Kenyon & Kenyon

(57) ABSTRACT

Provided are crystalline and amorphous form of valsartan, and processes for their preparation.

2 Claims, 24 Drawing Sheets

DSC curve of Valsartan purely amorphous.

POLYMORPHS OF VALSARTAN

PRIORITY

This application is a divisional application of U.S. patent application Ser. No. 10/802,627 filed Mar. 17, 2004, which claims the benefit of U.S. provisional application Ser. No. 60/473,640, filed May 28, 2003, and U.S. provisional application Ser. No. 60/455,286, filed Mar. 17, 2003, the contents of all of which are incorporated herein.

FIELD OF THE INVENTION

The present invention relates to the solid state chemistry of valsartan.

BACKGROUND OF THE INVENTION

Valsartan, also known as (S)-N-(1-Carboxy-2-methyl-prop-1-yl)-N-pentanoyl-N-[2'-(1H-tetrazol-5-yl)bi phenyl-4-ylmethyl]-amine, has the following structure:

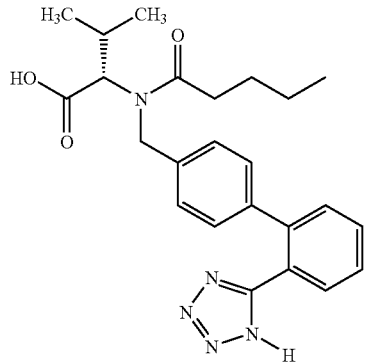

and is marketed as the free acid under the name DIOVAN. DIOVAN is prescribed as oral tablets in dosages of 40 mg, 80 mg, 160 mg and 320 mg of valsartan.

Valsartan and/or its intermediates are disclosed in various references, including: U.S. Pat. Nos. 5,399,578, 5,965,592, 5,260,325, 6,271,375, WO 02/006253, WO 01/082858, WO 99/67231, WO 97/30036, Peter Bühlmayer, et. al., Bioorgan. & Med. Chem. Let., 4(1) 29–34 (1994), Th. Moenius, et. al., J. Labelled Cpd. Radiopharm., 43(13) 1245–1252 (2000), and Qingzhong Jia, et. al., Zhongguo Yiyao Gongye Zazhi, 32(9) 385–387 (2001), all of which are incorporated herein by reference.

Valsartan is an orally active specific angiotensin II antagonist acting on the AT1 receptor subtype. Valsartan is prescribed for the treatment of hypertension. U.S. Pat. No. 6,395,728 is directed to use of valsartan for treatment of diabetes related hypertension. U.S. Pat. Nos. 6,465,502 and 6,485,745 are directed to treatment of lung cancer with valsartan. U.S. Pat. No. 6,294,197 is directed to solid oral dosage forms of valsartan. These patents are incorporated herein by reference.

The present invention relates to the solid state physical properties of valsartan. These properties can be influenced by controlling the conditions under which valsartan is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by powder X-ray crystallography, solid state $^{13}C$ NMR spectrometry and infrared spectrometry.

U.S. Pat. No. 5,399,578, incorporated herein by reference, in Example 16, obtains valsartan and discloses: "melting interval 105–115 (from ethyl acetate)."

In the Merck Index (12-th edition, p. 1691, valsartan n. 10051), valsartan is described as "crystals from diisopropyl ether, mp 116–117° C." The Merck Index may be reciting the product of example 37 of EP 0 443 983, which is in German. The product is not otherwise characterized by the Merck Index.

In J. of Labeled compounds and radiopharmaceuticals 2000, 43, 1245–1252 on page 1249 (synthesis of [$^{14}C_2$] valsartan 2), there is a description of the preparation of valsartan by crystallization from a 1:1 mixture of ethyl-acetate and Hexane. Repetition of this procedure led to a sample with X-Ray powder diffraction pattern as depicted in FIG. 1 (bottom pattern). The pattern in FIG. 1 shows a diffuse X-Ray diffraction, which indicates presence of an amorphous material.

WO 02/06253 also discloses amorphous form of valsartan: "The X-ray diffraction diagram consists essentially of a very broad, diffuse X-ray diffraction; the free acid is therefore characterized as almost amorphous under X-ray. The melting point linked with the measured melting enthalpy of 12 kJ/mol [approximately 28 j/g] unequivocally confirm the existence of a considerable residual arrangement in the particles or structural domains for the free acid valsartan. There is a need for more stable, e.g. crystalline forms of valsartan." The WO 02/06253 then goes on to disclose salts of valsartan in crystalline form.

There is a need in the art for crystalline valsartan in the free acid form. There is also a need in the art for purely amorphous valsartan, which does not undergo "a considerable residual arrangement in the particles or structural domains." There is also a need in the art for additional processes for preparation of amorphous form.

SUMMARY OF THE INVENTION

In one aspect, the present invention provides a process for preparing amorphous form of valsartan comprising the steps of precipitating amorphous valsartan from a solution of valsartan in a solvent selected from the group consisting of methyl t-butyl ether and acetone and recovering valsartan amorphous form.

In another aspect, the present invention provides a process for preparing amorphous form of valsartan comprising the steps of precipitating amorphous valsartan from a mixture of water and a solvent selected from the group consisting of ethanol, DMF, acetone and mixtures thereof and recovering the precipitated amorphous valsartan In another aspect, the present invention provides a process for preparing amorphous form of valsartan comprising the steps of preparing a solution of valsartan in a solvent selected from the group consisting of tetrahydrofuran, dioxane, ethanol, isopropanol, diethyl ether and methanol and removing the solvent.

In another aspect, the present invention provides a process for preparing amorphous form of valsartan comprising the steps of suspending valsartan in a solvent selected from the group consisting of water and $C_5$ to $C_{12}$ saturated hydrocarbon to obtain amorphous valsartan and recovering the amorphous valsartan.

In another aspect, the present invention provides a process for preparing amorphous form of valsartan comprising the steps of acidifying a basic aqueous solution of valsartan, wherein the acidifying results in precipitation of amorphous valsartan and recovering the precipitated amorphous valsartan.

In another aspect, the present invention provides a process for preparing amorphous form of valsartan comprising the steps of heating valsartan in diisopropyl ether to obtain amorphous valsartan and recovering the amorphous valsartan.

In another aspect, the present invention provides a process for preparing amorphous valsartan comprising the step of heating a crystalline form of valsartan selected from the group consisting of Form III or Form VII.

In another aspect, the present invention provides amorphous form of valsartan, wherein the amorphous form has a DSC thermogram that lacks a melting point above about 1 J/g.

In another aspect, the present invention provides a process for preparing the crystalline valsartan (Form I) having an XRPD pattern with peaks at 5.4, 13.0, 16.3, 19.5, 20.7, 23.4±0.2 degrees 2-theta comprising the steps of heating a solution of valsartan in a solvent selected from the group consisting of methyl ethyl ketone and ethyl acetate, cooling the solution to a temperature of about negative 20° C. to about 20° C. to induce crystallization and recovering the crystalline valsartan without heating.

In another aspect, the present invention provides a crystalline valsartan (Form II) characterized by an XRPD pattern with peaks at 5.8, 12.7, 14.0, 17.6, 20.8, 22.5±0.2 degrees 2-theta, and a process for preparing the crystalline valsartan comprising the steps of crystallizing the crystalline valsartan from an emulsion or solution of valsartan in a $C_5$ to $C_{12}$ aromatic hydrocarbon and recovering the crystalline valsartan.

In another aspect, the present invention provides for a crystalline valsartan (Form III) with an XRPD pattern with peaks at 5.1, 10.1, 15.3, 18.6±0.2 degrees 2-theta, which may be prepared by a process for preparing crystalline valsartan comprising the steps of crystallizing the crystalline valsartan from a solution of valsartan in t-butyl acetate and recovering the crystalline valsartan.

In another aspect, the present invention provides a crystalline valsartan (Form IV) having an XRPD pattern with peaks at 6.2, 10.7, 14.5, 15.7, 19.0, 23.5, 24.8±0.2 degrees 2-theta, which may be prepared by a process comprising the steps of crystallizing the crystalline valsartan from a solution of valsartan in acetonitrile and recovering the crystalline valsartan.

In another aspect, the present invention provides a crystalline valsartan (Form VI) characterized by an XRPD pattern with peaks at 5.5, 13.3, 14.3, 17.7, 21.1, 22.3±0.2 degrees 2-theta, which may be prepared by heating crystalline valsartan Form VII.

In another aspect, the present invention provides a crystalline valsartan (Form VII) characterized by an XRPD pattern with peaks at 5.2, 15.2, 15.9, 18.6, 22.8, 23.6±0.2 degrees 2-theta, which may be prepared by a process comprising the steps of crystallizing the crystalline valsartan from a solution of valsartan in a solvent selected from the group consisting of 2-hexanone and n-butyl acetate and recovering the crystalline valsartan.

In another aspect, the present invention provides a crystalline valsartan (Form VIII) characterized by an XRPD pattern with peaks at about 5.7, 13.6, 18.0±0.2 degrees 2-theta, which may be prepared by heating crystalline valsartan Form I.

In another aspect the present invention provides for a crystalline valsartan (Form IX) characterized by an XRPD pattern with peaks at 6.3, 14.0, 17.9±0.2 degrees 2-theta, which may be prepared by a process comprising the step of heating crystalline valsartan Form IV, or a process comprising the steps of crystallizing the crystalline valsartan from a solution of valsartan in nitromethane and recovering the crystalline valsartan, or a process comprising the steps of crystallizing the crystalline valsartan from a solution of valsartan in acetonitrile, recovering the crystalline valsartan and heating the crystalline valsartan.

In another aspect, the present invention provides for a crystalline form of valsartan (Form X), wherein the crystalline form is characterized by an XRD pattern with peak at 5.6±0.2 degrees 2 theta and with two broad peaks at 15.0 and 20.6 degrees 2 theta, and a process for its preparation comprising the steps of preparing a solution of valsartan n-butyl acetate, crystallizing the crystalline form from the solution and recovering the crystalline form.

In another aspect, the present invention provides a crystalline form of Valsartan, wherein the crystalline form (Form XI) is characterized by an XRD pattern with peaks at 5.2, 10.5, 12.9, 13.9, 18.8±0.2 degreeS 2 theta, and a process for its preparation comprising the steps of contacting a crystalline form of valsartan with toluene to obtain a transformation in the crystalline form.

In another aspect, the present invention provides a process for preparing amorphous valsartan comprising the steps of preparing a solution of valsartan in ethyl acetate, cooling the solution, recovering a solid from the ethyl acetate and drying the solid to obtain amorphous valsartan.

In another aspect, the present invention provides a process for preparing amorphous valsartan comprising the step of heating crystalline valsartan Form I.

In another aspect, the present invention provides a process for preparing amorphous valsartan comprising the steps of contacting a crystalline form of valsartan with hexane vapor atmosphere to obtain a crystalline transformation, and recovering the transformed crystalline form.

In another aspect, the present invention provides a crystalline form of Valsartan (Form XIII), wherein the crystalline form is characterized by an XRD pattern with peaks at 5.1, 11.6, 15.8, 18.6, 26.2±0.2 degrees 2 theta, and a process for its preparation comprising the steps of contacting valsartan in solid state with a water vapor atmosphere to obtain a transformation to the crystalline form.

In another aspect, the present invention provides a pharmaceutical composition comprising valsartan in the solid state with a thermogram lacking a melting point above about 1 J/g, and a pharmaceutically acceptable excipient, and a method for treating hypertension in a mammal by administering the pharmaceutical composition.

In another aspect, the present invention provides a pharmaceutical composition comprising a crystalline valsartan selected from the group consisting of Form II, III, IV, VI, VII, VIII, IX, X, XI and XIII, and a pharmaceutically acceptable excipient, and methods for treating hypertension with such composition.

In one aspect, the present invention provides valsartan in the solid state, having an XRPD pattern with visible diffraction pattern from about 5 to about 30 degrees two theta and a DSC thermogram with at least a single melting point, wherein the crystalline form contains about 15% to about 65% crystalline valsartan relative to amorphous form. Preferably, the area percentage is of about 40% to about 65%, more preferably of about 50% to about 60%. In another aspect, a valsartan in the solid state is provided containing at least about 15% crystalline valsartan, more preferably at least about 30%, relative to amorphous form.

DETAILED DESCRIPTION OF THE INVENTION

Figure 1:
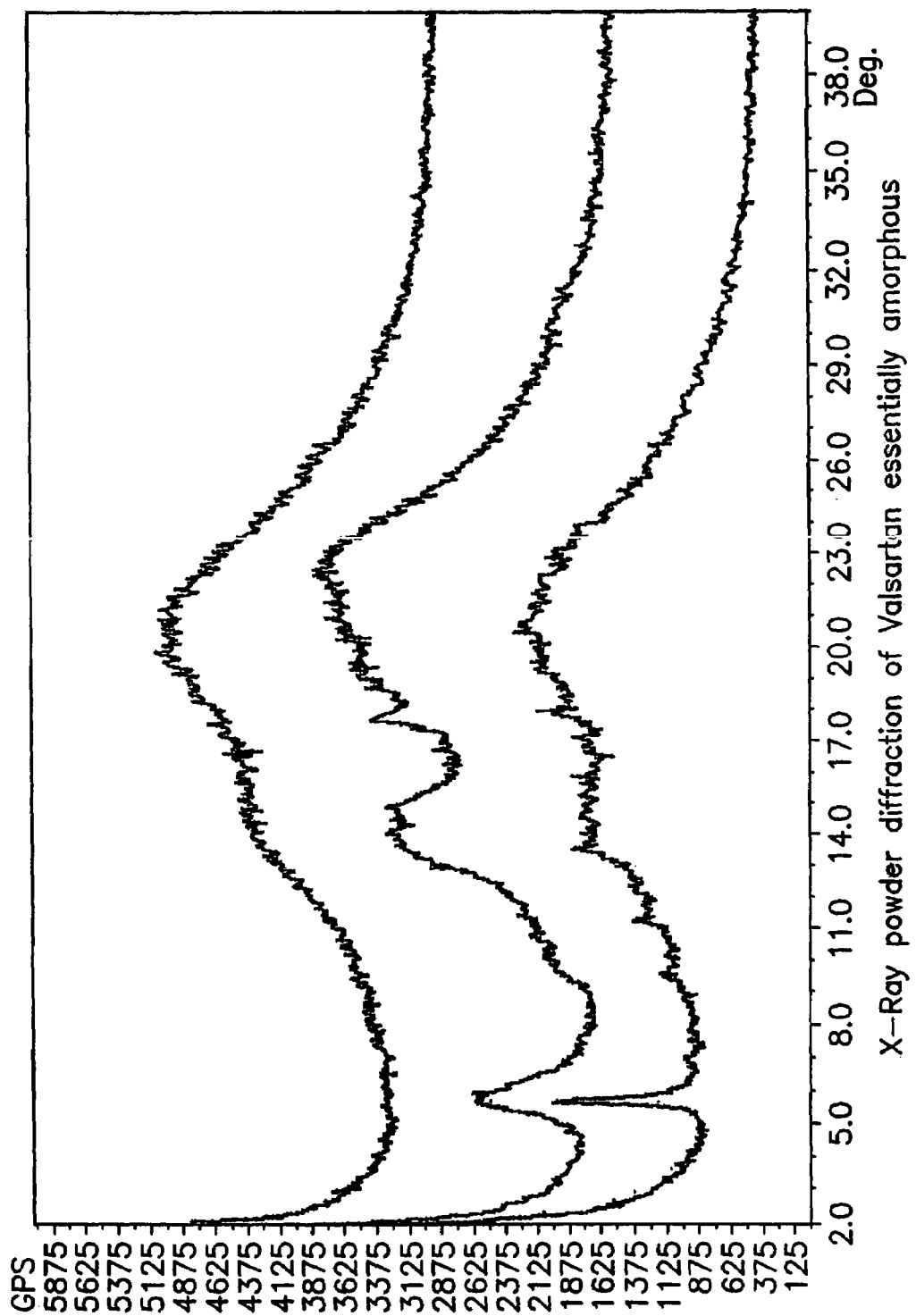
FIG. 1 is three different X-Ray powder diffraction ("XRPD") patterns of valsartan essentially amorphous.

As used herein, the term drying refers to removal of solvent through application of heat, preferably carried out under ambient or reduced pressure.

As used herein, the term reduced pressure refers to a pressure below one atmosphere, more preferably below about 100 mmHg.

As used herein, the term precipitation refers to formation of a suspension of small solid particles in a mixture.

As used herein, the term crystallization refers to a process for forming crystals from a liquid or gas.

As used herein, an anti-solvent is a liquid that when added to a solution of X in the solvent, induces precipitation of X. Precipitation of X is induced by the anti-solvent when addition of the anti-solvent causes X to precipitate from the solution more rapidly or to a greater extent than X precipitates from a solution containing an equal concentration of X in the same solvent when the solution is maintained under the same conditions for the same period of time but without adding the anti-solvent. Precipitation can be perceived visually as a clouding of the solution or formation of distinct particles of X suspended in the solution or collected at the bottom the vessel containing the solution.

As used herein, the term $C_5$ to $C_{12}$ saturated hydrocarbon refers to a straight/branched and/or cyclic/acyclic hydrocarbon. Preferred hydrocarbons are cyclohexane, cycloheptane, cyclohexane, n-heptane and n-hexane, with n-hexane and n-heptane being preferred. The terms hexane and heptane used hereinafter refer to n-hexane and n-heptane.

As used herein, the term $C_5$ to $C_{12}$ aromatic hydrocarbon refers to substituted and unsubstituted hydrocarbons having a phenyl group as its backbone. Preferred hydrocarbons include benzene, xylene and toluene, with toluene being more preferred.

As used herein, the term "trituration" refers to a heterogeneous mixture of valsartan in a solvent, wherein complete dissolution does not take place.

The present invention provides for different crystalline forms of valsartan, denominated Form I, II, III, IV, VI, VII, VIII, IX, X, XI and XIII. Crystalline valsartan is characterized by having a strong peak in the range 5–7 degrees 2-theta, and visible diffraction peaks in the range 8–30 degrees 2-theta. Moreover, the strong diffraction peak in the range 5–7 degrees 2 theta has a half-height width of about 1.0 degree, more preferably about 0.5 degree, most preferably about 0.3 degree.

In one aspect, the present invention provides for crystalline Form I of valsartan. Valsartan Form I is characterized by an X-Ray diffraction pattern with peaks at 5.4, 13.0, 16.3, 19.5, 20.7, 23.4±0.2 degrees 2-theta. Additional XRPD peaks are listed in Table I.

Valsartan Form I may be crystallized out of a solution of valsartan in ethylacetate or methyl ethyl ketone. A solution of valsartan in ethyl acetate or methyl ethyl ketone is prepared, preferably at reflux temperature. The solution is cooled to induce crystallization. Preferably the solution is cooled to a temperature of from about −20° C. to about 20° C., more preferably from about −10° C. to about 10° C. The resulting crystals may then be recovered by techniques well known in the art, such as filtration, centrifugation, decanting, etc. The crystals are not heated to avoid a transition to other polymorphic forms.

In another aspect, the present invention provides for crystalline valsartan Form II. Valsartan Form II is characterized by an X-Ray diffraction pattern with peaks at 5.8, 12.7, 14.0, 17.6, 20.8, 22.5±0.2 degrees 2-theta. Additional XRPD peaks are listed in Table I.

Valsartan Form II may be prepared by crystallization from a mixture of a $C_5$ to $C_{12}$ hydrocarbon, such as toluene, and valsartan, e.g., solution or emulsion. Form II is obtained from processes where the original crystalline form used is lost, such as an emulsion. In one embodiment, valsartan is added to toluene, and the temperature is increased to melt the valsartan. Preferably, the mixture of valsartan in toluene is heated to a temperature that allows for formation of the emulsion, more preferably about reflux temperature. Preferably the emulsion is cooled to a temperature of from about −20° C. to about 20° C., more preferably from about −10° C. to about 10° C. The resulting crystals may then be recovered by techniques well known in the art, such as filtration, centrifugation, decanting, etc.

The crystals may then be dried. Drying may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient.

In another aspect, the present invention provides for crystalline valsartan Form III. Valsartan Form III is characterized by an X-Ray diffraction pattern with peaks at 5.1, 10.1, 15.3, 18.6±0.2 degrees 2-theta. Additional XRPD peaks are listed in Table I.

Valsartan Form III is obtained by crystallization from t-butyl acetate. A solution of valsartan in t-butyl acetate is prepared. The solution may be cooled to induce crystallization. Preferably the solution is cooled to a temperature of from about −20° C. to about 20° C., more preferably from about −10° C. to about 10° C. The resulting crystals may then be recovered by techniques well known in the art, such as filtration, centrifugation, decanting, etc.

In another aspect, the present invention provides for crystalline valsartan Form IV. Valsartan Form IV is characterized by an X-Ray diffraction pattern with peaks at 6.2, 10.7, 14.5, 15.7, 19.0, 23.5, 24.8±0.2 degrees 2-theta. Additional XRPD peaks are listed in Table I.

Valsartan Form IV may be prepared by crystallization from acetonitrile. A solution of valsartan in acetonitrile is prepared. The solution may be cooled to induce crystallization. Preferably the solution is cooled to a temperature of from about −20° C. to about 20° C., more preferably from about −10° C. to about 10° C. The resulting crystals may then be recovered by techniques well known in the art, such as filtration, centrifugation, decanting, etc.

In another aspect the present invention provides for crystalline valsartan Form VII. Valsartan Form VII is characterized by an XRPD pattern with peaks at 5.2, 15.2, 15.9, 18.6, 22.8, 23.6±0.2 degrees 2-theta. Additional XRPD peaks are listed in Table I.

Valsartan Form VII may be crystallized out of 2-hexanone or n-butyl acetate. A solution of valsartan in 2-hexanone or n-butyl acetate is prepared. The solution may be cooled to induce crystallization. Preferably the solution is cooled to a temperature of from about −20° C. to about 20° C., more preferably from about −10° C. to about 10° C. The resulting crystals may then be recovered by techniques well known in the art, such as filtration, centrifugation, decanting, etc.

In another aspect, the present invention provides for crystalline valsartan Form VI. Valsartan Form VI is characterized by an XRPD pattern with peaks at 5.5, 13.3, 14.3, 17.7, 21.1, 22.3±0.2 degrees 2-theta. Additional XRPD peaks are listed in Table I.

Valsartan Form VI may be prepared by heating crystals of Form VII, preferably those obtained by crystallization out of 2-hexanone. Drying, which uses heat, may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient to induce a transition.

In another aspect, the present invention provides for crystalline valsartan Form VIII. Valsartan Form VIII is characterized by an X-Ray diffraction pattern with peaks at 5.7, 13.6, 18.0 5±0.2 degrees 2-theta. Additional XRPD peaks are listed in Table I.

Valsartan Form VIII may be prepared by heating the crystals of Form I, preferably the crystals obtained by crystallization from methyl ethyl ketone. Drying, which uses heat, may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient to induce a transition.

In another aspect, the present invention provides for crystalline valsartan Form IX. Crystalline valsartan Form IX is characterized by an X-Ray diffraction pattern with peaks at 6.3, 14.0, 17.9±0.2 degrees 2-theta. Additional XRPD peaks are listed in Table I.

Crystalline valsartan Form IX may be prepared by crystallization out of nitromethane. A solution of valsartan in nitromethane is prepared. The solution may be cooled to induce crystallization. Preferably the solution is cooled to a temperature of from about −20° C. to about 20° C., more preferably from about −10° C. to about 10° C. The resulting crystals may then be recovered by techniques well known in the art, such as filtration, centrifugation, decanting, etc.

The crystals may then be dried. Drying may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient.

Alternatively crystalline valsartan Form IX may be prepared by heating of Form IV, which is preferably prepared by crystallization out of acetonitrile. Drying, which uses heat, may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient to induce a transition.

The X-Ray diffraction peaks of the different forms of valsartan free acid are summarized in the following table. The numbers in bold represent the most characteristic peaks for each form.

TABLE I

| Form I | Form II | Form III | Form IV | Form VI | Form VII | Form VIII | Form IX |
|---|---|---|---|---|---|---|---|
| 5.4 | 5.8 | 5.1 | 6.2 | 5.5 | 5.2 | 5.7 | 6.3 |
| 9.8 | 12.7 | 10.1 | 10.7 | 10.0 | 9.5 | 7.0 | 9.9 |
| 10.6 | 14.0 | 15.3 | 12.3 | 10.8 | 10.4 | 9.6 | 10.9 |
| 13.0 | 16.1 | 18.6 | 13.0 | 12.3 | 11.6 | 11.5 | 14.0 |
| 14.0 | 17.6 | | 13.8 | 13.3 | 12.7 | 13.6 | 17.9 |
| 14.5 | 20.8 | | 14.5 | 14.3 | 13.8 | 17.1 | 18.9 |
| 14.9 | 22.5 | | 15.7 | 15.1 | 14.2 | 18.0 | 20.4 (broad) |
| 16.3 | 24.2 | | 16.3 | 17.7 | 14.8 | 19.3 | |
| 17.1 | 25.5 | | 18.5 | 19.3 | 15.2 | 20.7 | |
| 18.4 | 26.5 | | 19.0 | 20.0 | 15.9 | 22.2 | |
| 19.5 | | | 20.0 | 21.1 | 16.6 | 23.2 | |
| 20.7 | | | 20.5 | 22.3 | 18.0 | 23.9 | |
| 22.1 | | | 23.5 | 23.4 | 18.6 | | |
| 23.4 | | | 24.8 | 24.0 | 20.1 | | |
| 24.1 | | | | | 20.8 | | |
| | | | | | 22.1 | | |
| | | | | | 22.8 | | |
| | | | | | 23.2 | | |
| | | | | | 23.6 | | |
| | | | | | 24.4 | | |
| | | | | | 24.8 | | |
| | | | | | 26.1 | | |
| | | | | | 26.7 | | |
| | | | | | 28.3 | | |

The crystallinity of the different crystalline forms of valsartan, when calculated according to crystallinity function (By computing the ratio between the area of the crystalline peaks in the graph and the area of the whole graph) is as follows:

FORM I—~62% (Preferably from about 50% to about 70%)
FORM II—~63% (Preferably from about 50% to about 70%)
FORM III—~35% (Preferably from about 25% to about 45%)
FORM IV—~48% (Preferably from about 40% to about 60%)
FORM VI—~40% (Preferably from about 30% to about 50%)
FORM VII—~42% (Preferably from about 30% to about 50%)
FORM VIII—~17% (Preferably from about 10–15% to about 25%)
FORM IX—~29% (Preferably from about 20% to about 40%)

With the rest being amorphous.

The crystallinity index is measured quantitatively from the X-ray powder diffractogram by comparing the area of the crystalline peaks ($A_C$) to the area under the halo-shaped amorphous peak ($A_A$). Thus, ($A_C+A_A$) equals the total scattered intensity. The crystallinity index is represented by the formula: $CI=A_C*100/(A_C+A_A)$. CI is estimated at ±5%, due to fluctuation in the baseline.

Figure 20:
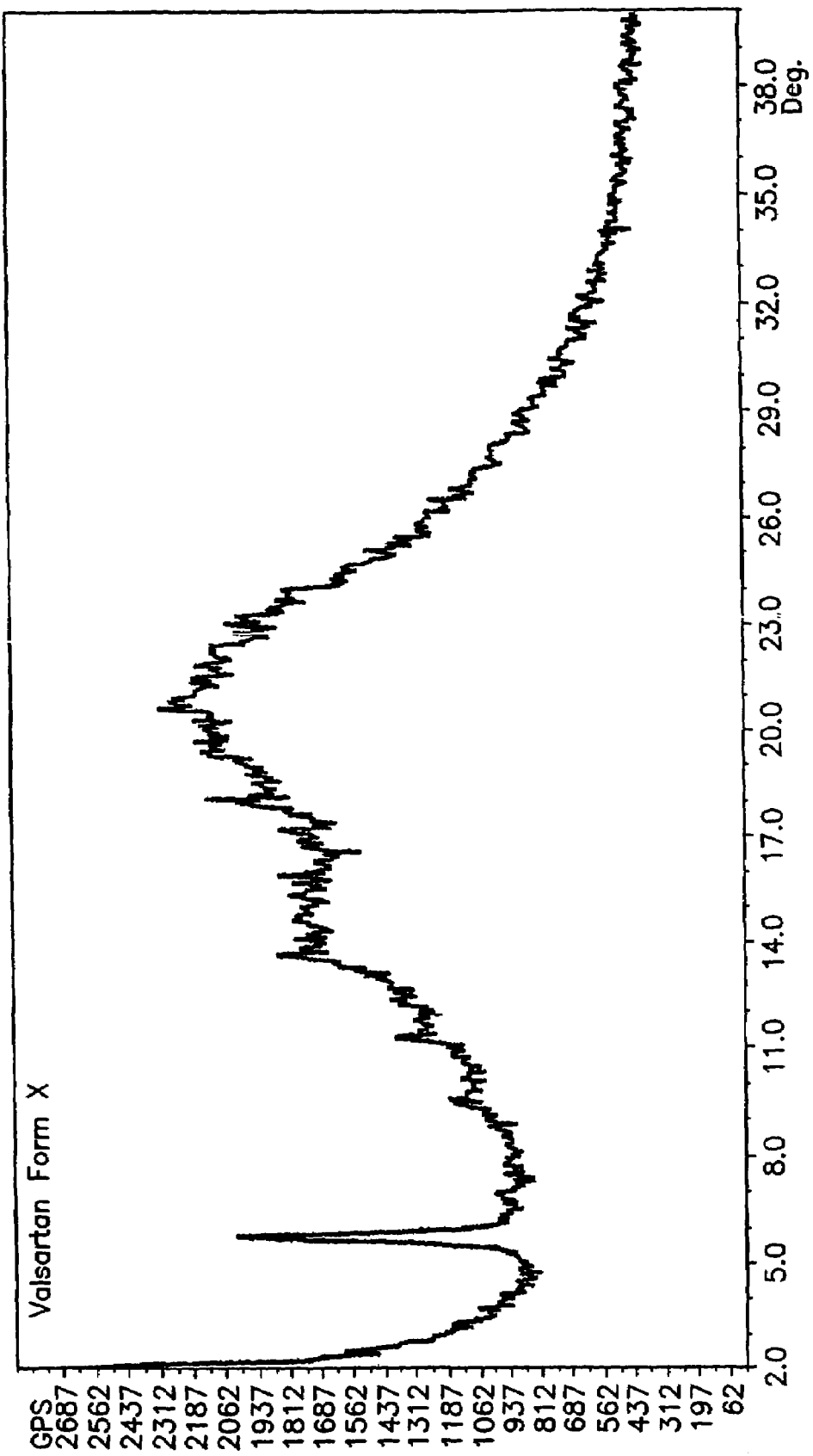
FIG. 20 is an X-Ray powder diffractogram of Valsartan Form X.

In another aspect, the present invention provides for crystalline valsartan Form X. Crystalline valsartan Form X is characterized by an XPD pattern (FIG. 20) with peak at 5.6±0.2 degrees 2 theta and with two broad peaks at 15.0 and 20.6±0.2 degrees 2 theta.

Form X may be prepared by crystallization out of n-butyl acetate. Preferably valsartan is heated to reflux temperature to obtain a solution. Crystallization is then induced by cooling to a temperature of about negative 10° C. to about 10° C., with 0° C. being most preferred. The wet crystalline form may be dried. Drying may be carried out under ambient or reduced pressure. Preferably, drying is carried out at a temperature of from about 40° C. to about 60° C., more preferably in combination with a pressure of less than about 30 mm Hg.

Figure 21:
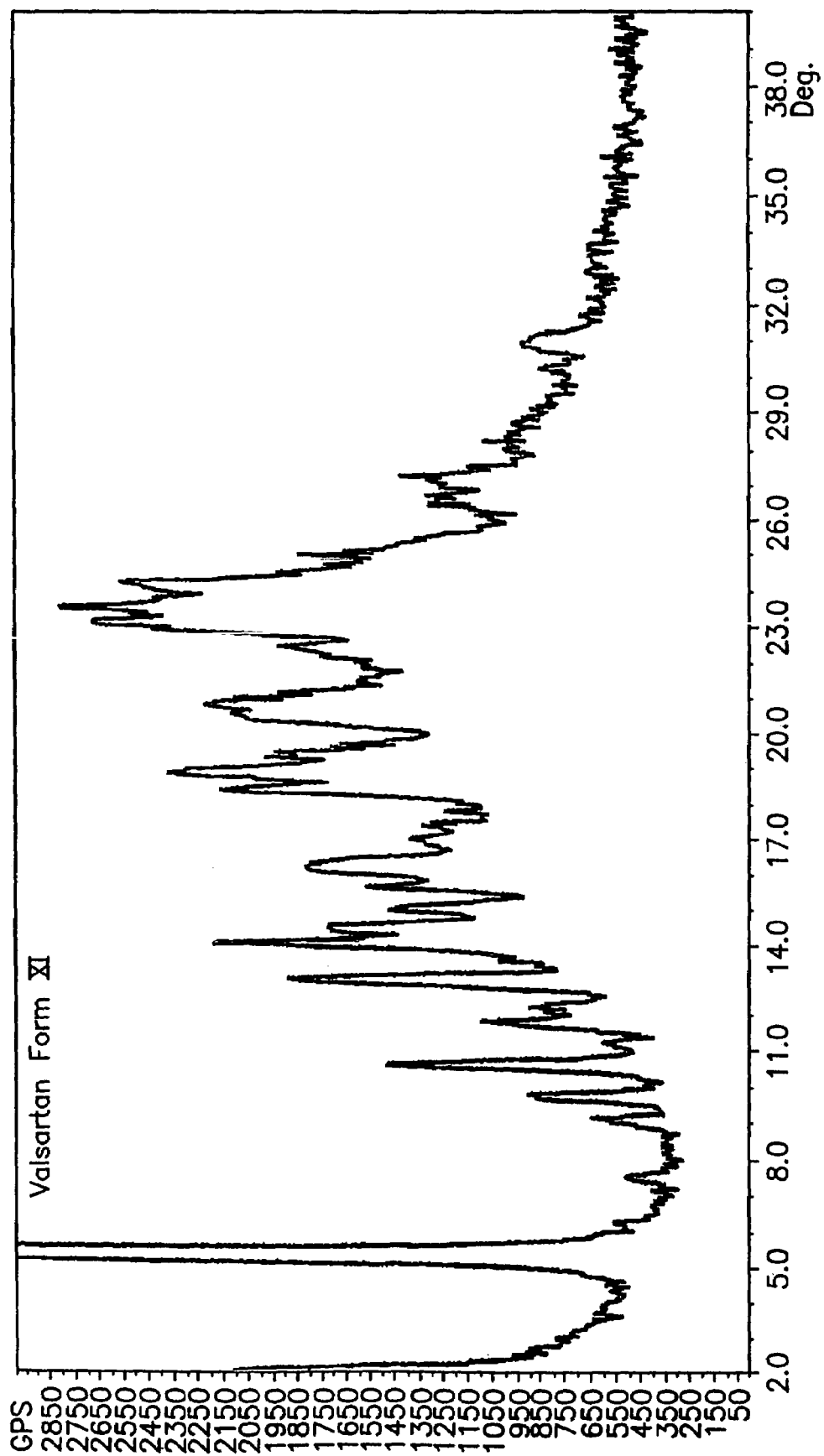
FIG. 21 is an X-Ray powder diffractogram of Valsartan Form XI.
Figure 22:
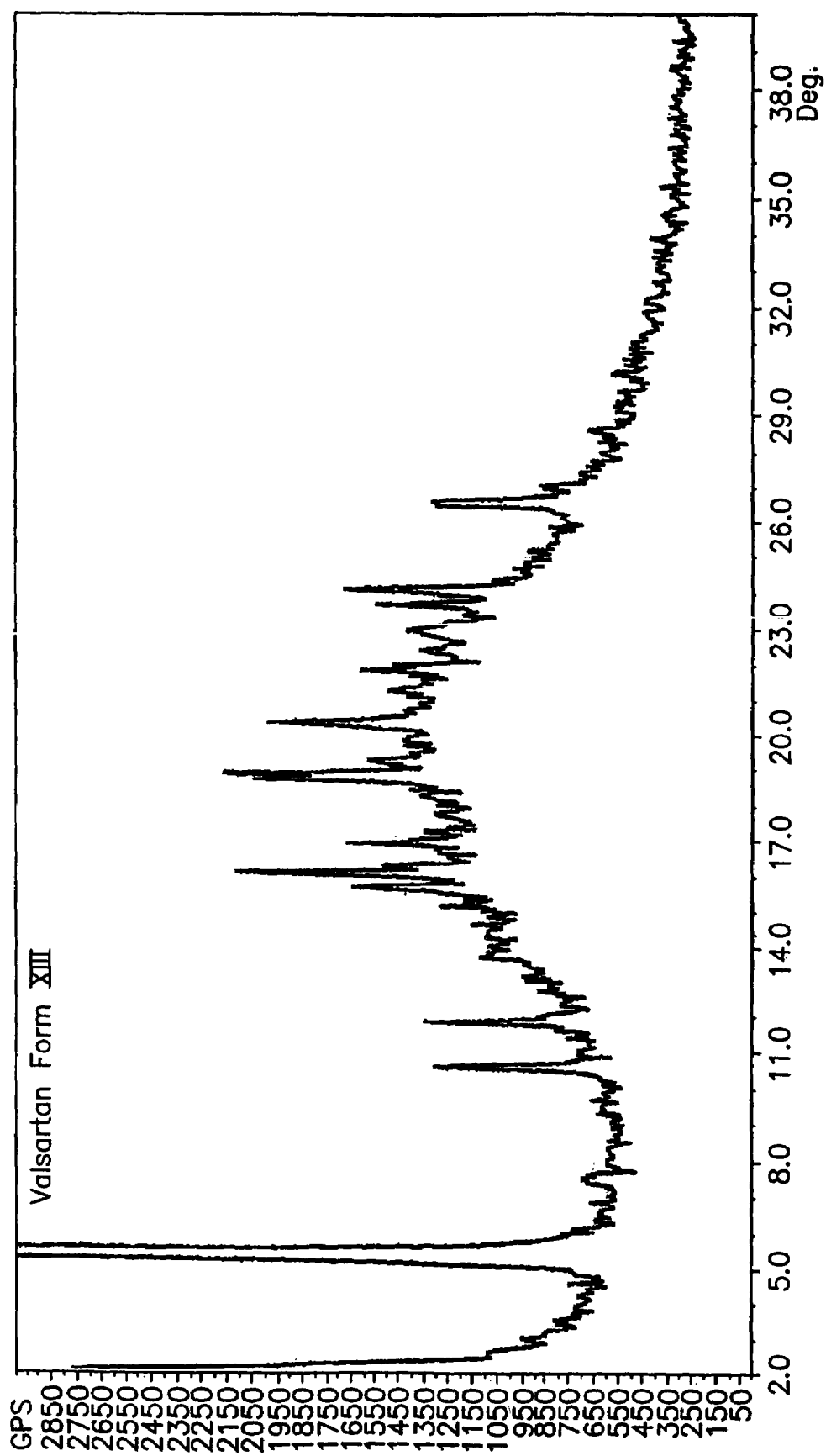
FIG. 22 is an X-Ray powder diffractogram of Valsartan Form XIII.

In another aspect, the present invention provides for crystalline valsartan Form XI. Crystalline valsartan Form XI is characterized by an XRD pattern (FIG. 21) with peak at 5.2, 10.5, 12.9, 13.9, 18.8±0.2 degrees 2 theta. Additional characteristic peaks are found at 9.7, 16.1, 20.7, 22.9, 24.1±0.2 degrees two-theta.

Valsartan Form XI may be prepared by contacting a crystalline form of valsartan with a $C_5$ to $C_{12}$ aromatic hydrocarbon, preferably toluene to obtain a transformation in the crystalline form. In one embodiment, the contacting is carried out by trituration, i.e., a heterogeneous mixture without complete dissolution. Preferably, the crystalline form triturated is Form II. The trituration may be carried out at a temperature of about 40° C. to about 60° C., followed by cooling to a temperature of about negative 10° C. to about 10° C. In another embodiment, the contacting is carried out by placing crystalline valsartan form in toluene vapor atmosphere. As used herein, an atmosphere of a particular solvent refers to air being saturated with at least about 50% of the vapors of the recited solvent. Two weeks of contact at room temperature is sufficient for transformation, though a lower amount of time may also be sufficient. Preferably the form placed in this atmosphere is Form VII. The transformation of the crystalline forms under these conditions points to the probability of Form XI being a solvate of toluene.

Figure 23:
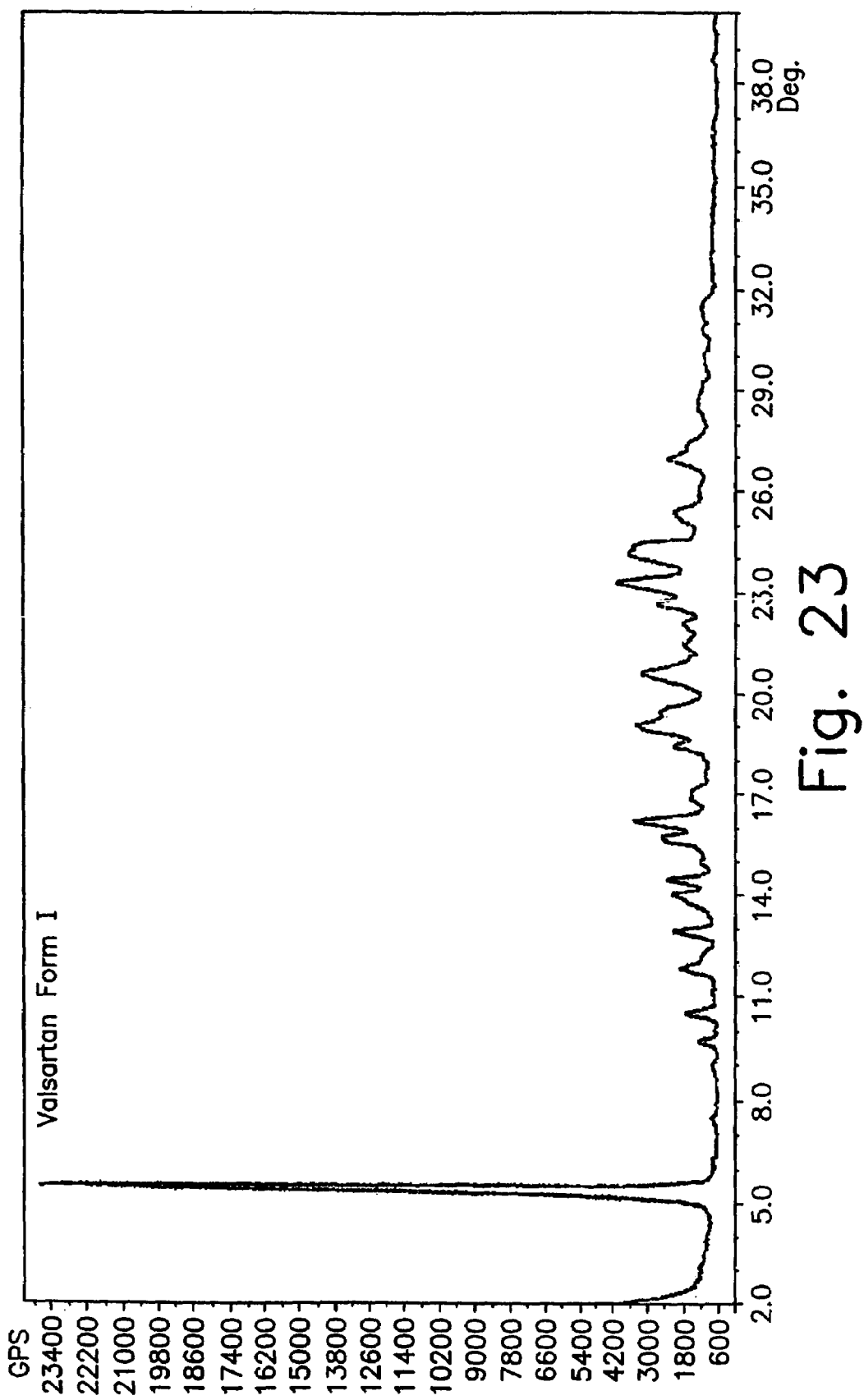
FIG. 23 is an X-ray powder diffractogram of valsartan Form I.
Figure 24:
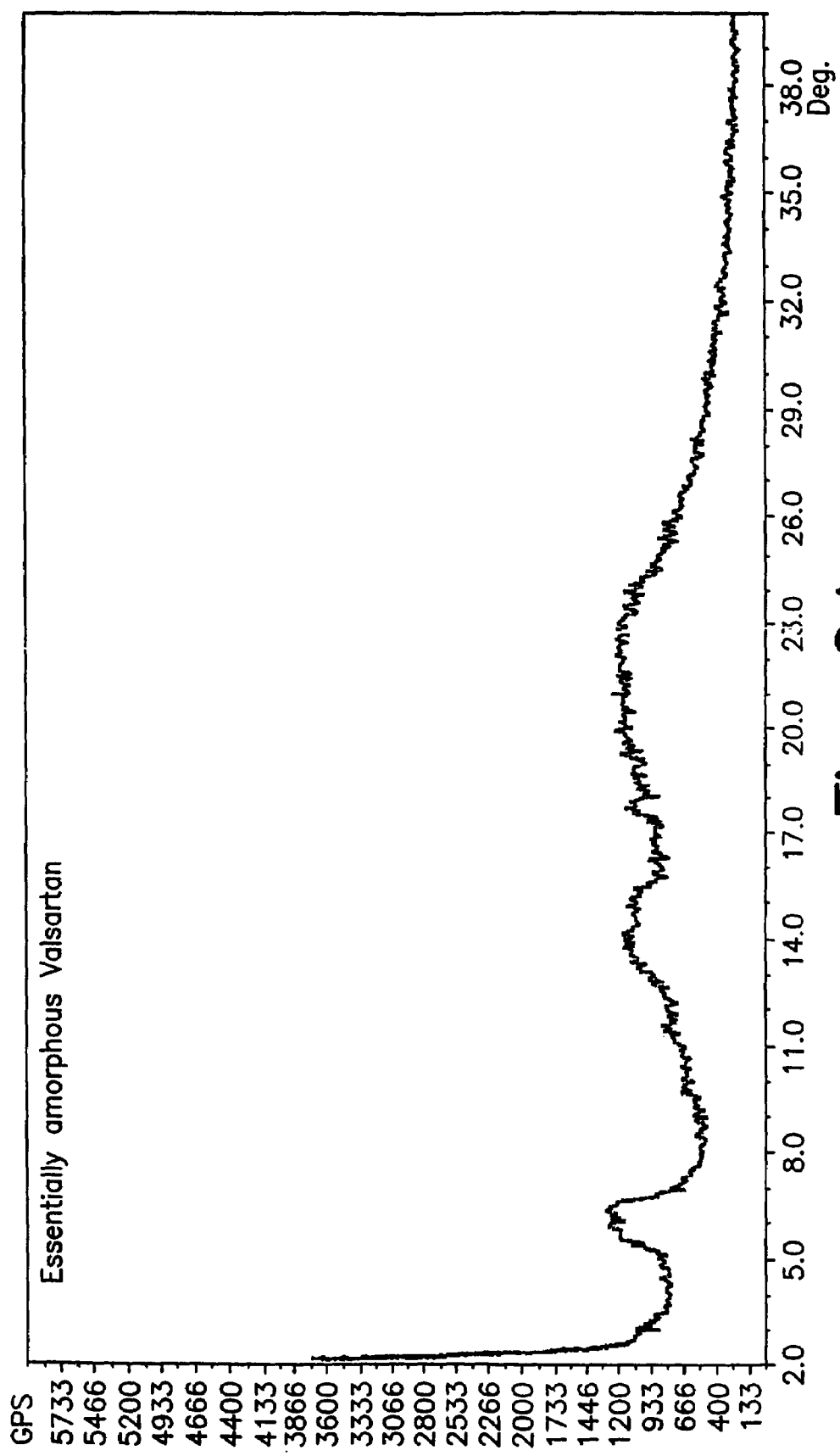
FIG. 24 is an X-ray powder diffractogram of valsartan essentially amorphous.

In another embodiment, the present invention provides for crystalline form XIII. Crystalline Form XIII is characterized by an XRD pattern (FIG. 23) with peaks at 5.1, 11.6, 15.8, 18.6, 26.2±0.2 degrees 2 theta. More preferably, the crystalline form is characterized by peaks at 10.4, 15.3, 16.4, 19.9, 23.8±0.2 degrees two-theta.

The present invention provides a process for preparing crystalline Valsartan Form XIII by contacting valsartan in solid state with a water vapor atmosphere to obtain the crystalline form. The valsartan contacted is preferably Form III, VI, VII, VIII, IX, X, XI, XIII and amorphous form. Two weeks of contact at room temperature is sufficient for transformation, though a lower amount of time may also be sufficient. The transformation of the crystalline form under these conditions points to the probability of the crystalline form being a hydrate.

In another aspect, the present invention provides for obtaining amorphous valsartan by precipitation out of organic solvents such as acetone, methyl t-butyl ether, a mixture of water and ethanol, a mixture of water and DMF and a mixture of water and acetone.

A solution of valsartan in the above solvents is prepared. The solution may be cooled to induce crystallization. Preferably the solution is cooled to a temperature of from about −20° C. to about 20° C., more preferably from about −10° C. to about 10° C. The resulting precipitate may then be recovered by techniques well known in the art, such as filtration, centrifugation, decanting, etc.

Water is used as an anti-solvent in the above mixtures to precipitate valsartan, since valsartan is substantially insoluble in water. Preferably, water is added slowly to a prepared solution of valsartan in the solvent, more preferably with vigorous stirring. One of skill in the art may appreciate that the solvent and the anti-solvent may be combined in different manner, and the exact order of addition of the solvent to the anti-solvent may not make a difference in the final result. Crystallization from a binary mixture may also be possible.

Alternatively, amorphous valsartan may be prepared by removing a solvent from the solution of valsartan in an organic solvent. The solvents used are preferably THF, dioxane, ethanol, isopropanol, diethylether and methanol. A solution of valsartan in the above solvents is prepared, followed by solvent removal. Preferably, removing is carried out by evaporation. Evaporating/drying may be carried out under ambient or reduced pressure. Preferably, evaporating/drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient.

In a preferred embodiment, excess solvent is first removed by evaporation under reduced pressure, followed by drying at an elevated temperature.

In another embodiment, amorphous form is prepared by precipitation from an aqueous acidic solution. A solution of valsartan in an aqueous basic solution is prepared. The aqueous basic solution may be that of an alkali metal or alkaline earth metal salt such as NaOH, KOH or potassium carbonate. Preferably, the pH of the solution is above about 10, more preferably about 12. An acid is then added to reduce the pH, resulting in precipitation. Preferably, the resulting pH is from about 2 to about 5. The pH may be adjusted by using aqueous acidic solutions of inorganic acids such as HCl, sulfuric acid, formic acid and acetic acid.

Amorphous form of valsartan may also be prepared by heating a mixture of valsartan in diisopropyl ether followed by drying. The mixture is preferably heated from about 50° C. to about reflux temperature. After heating, a gummy material is obtained which has to be dried, as described above, to obtain desirable amorphous form. Drying may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient.

In another embodiment, amorphous valsartan is obtained from a mixture, such as by suspension in a solvent. Valsartan is suspended in a $C_5$ to a $C_{12}$ hydrocarbon such as heptane or cyclohexane, or in water or mixtures thereof. The suspension may be heated to a desirable temperature depending on the solvent (preferably about 35° C. to about 55° C. for water, and about 60° C. to about 80° C. for heptane and cyclohexane). A solid may then be recovered as amorphous form by techniques well known in the art, such as filtration, centrifugation, decanting, etc. Before recovery, the suspension may be cooled. Preferably the suspension is cooled to a temperature of from about −20° C. to about 20° C., more preferably from about −10° C. to about 10° C.

Amorphous valsartan may also be prepared by contacting a crystalline form of valsartan with a vapor atmosphere of hexane to obtain a crystalline transformation. Two weeks of contact at room temperature is sufficient for transformation, though a lower amount of time may also be sufficient. Preferably the forms contacted with such atmosphere include Form VI and Form VII.

Amorphous form may also be prepared by drying various crystalline forms of valsartan. Drying of Forms I, III and VII results in amorphous form. The Form VII used as s starting material is preferably that obtained by crystallization out of n-butyl acetate. Drying may be carried out under ambient or reduced pressure. Preferably, drying is carried out at a temperature of from about 40° C. to about 60° C., more preferably in combination with a pressure of less than about 30 mm Hg. Approximately a few hours of drying, e.g. about 2 to about 5 hours, depending on the conditions, may be sufficient for transition.

Depending on the process used, the amorphous material may be substantially free of crystalline impurities, or contain substantial amounts of crystalline impurities. Amorphous material containing substantial amounts of crystalline materials as impurities is hereby referred to as "valsartan essentially amorphous." As illustrated in FIG. 1, the presence of crystalline impurities does not allow for a good halo shape pattern typical of amorphous form that is substantially free of crystalline material. If the amount of the crystalline impurities is low, it is possible that the crystals would not be detected by an XRD, but the presence of the crystals even in low amounts results in the presence of a peak in the DSC thermogram.

Figure 2:
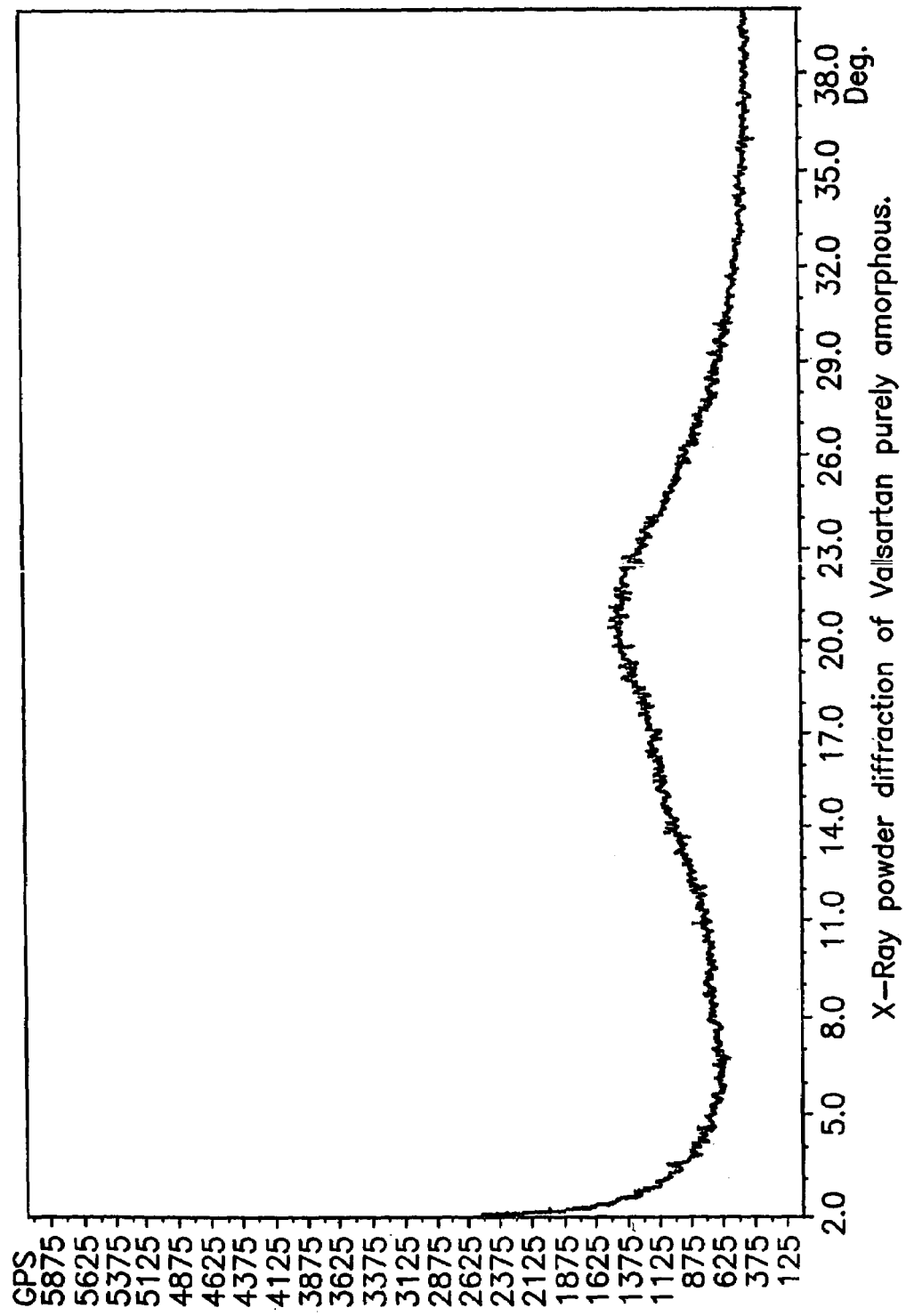
FIG. 2 is an X-Ray powder diffraction of valsartan purely amorphous.
Figure 3:
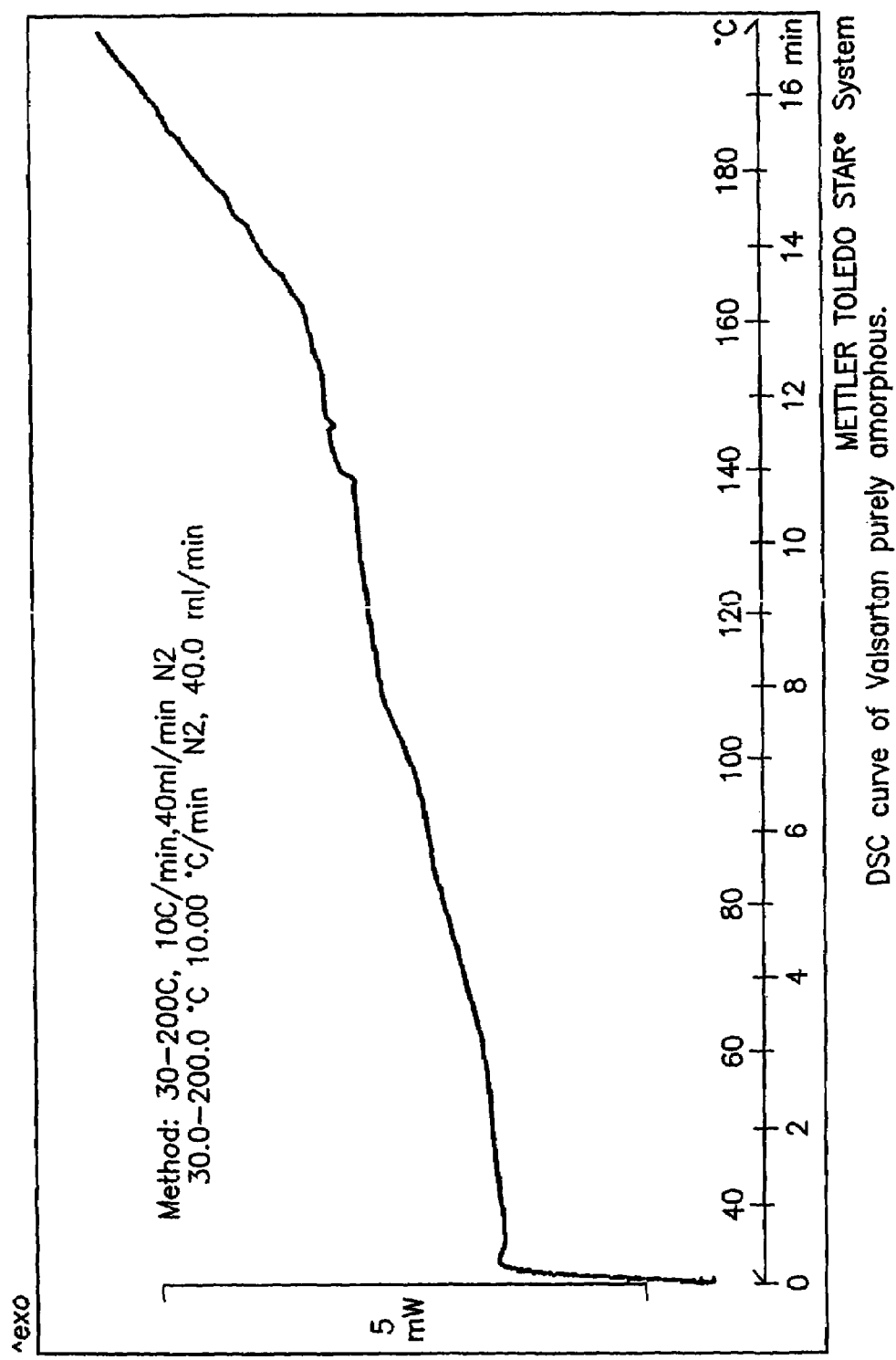
FIG. 3 is a DSC thermogram of valsartan purely amorphous.
Figure 4:
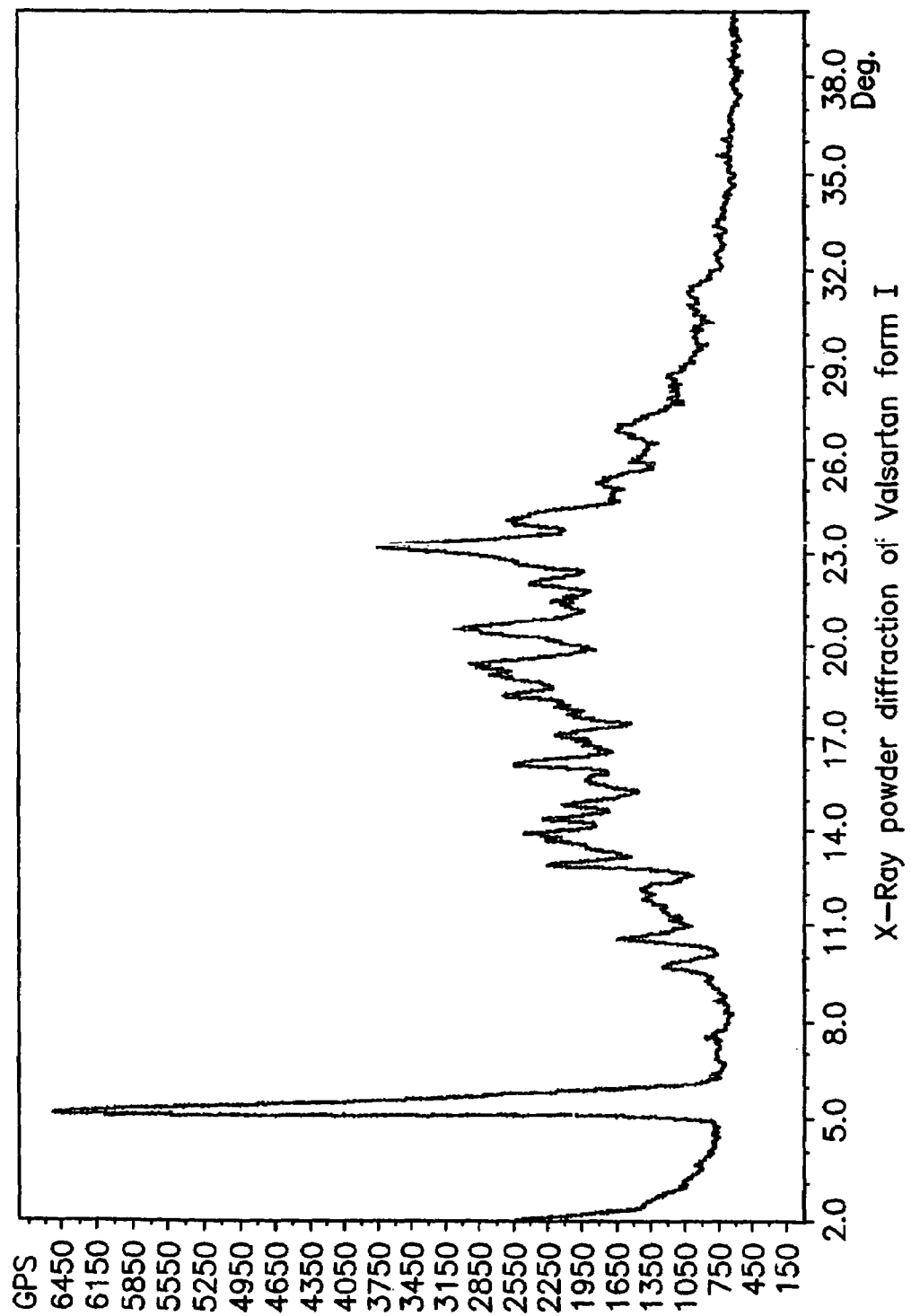
FIG. 4 is an X-Ray powder diffraction of valsartan Form I.
Figure 5:
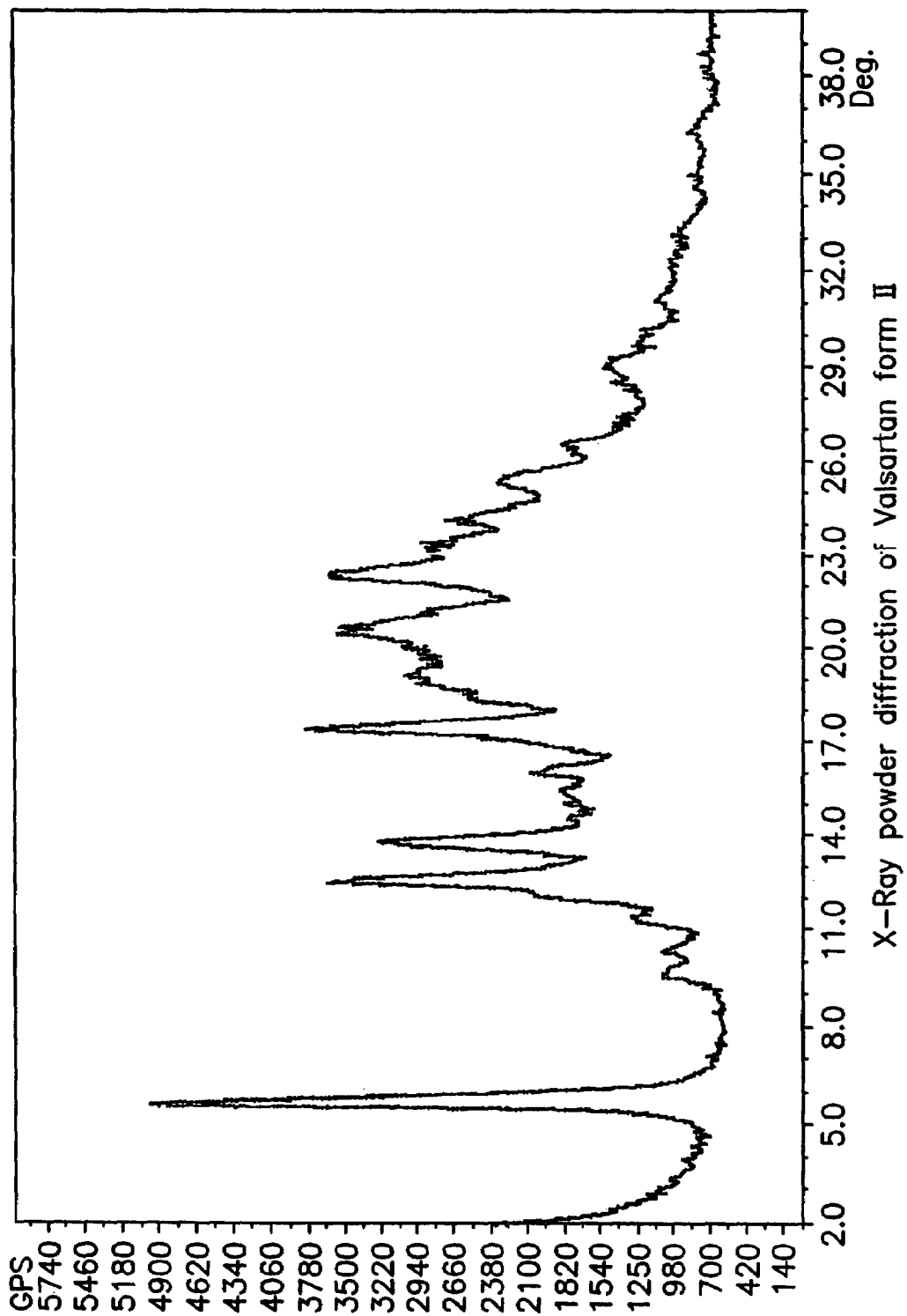
FIG. 5 is an X-Ray powder diffraction of valsartan Form II.
Figure 6:
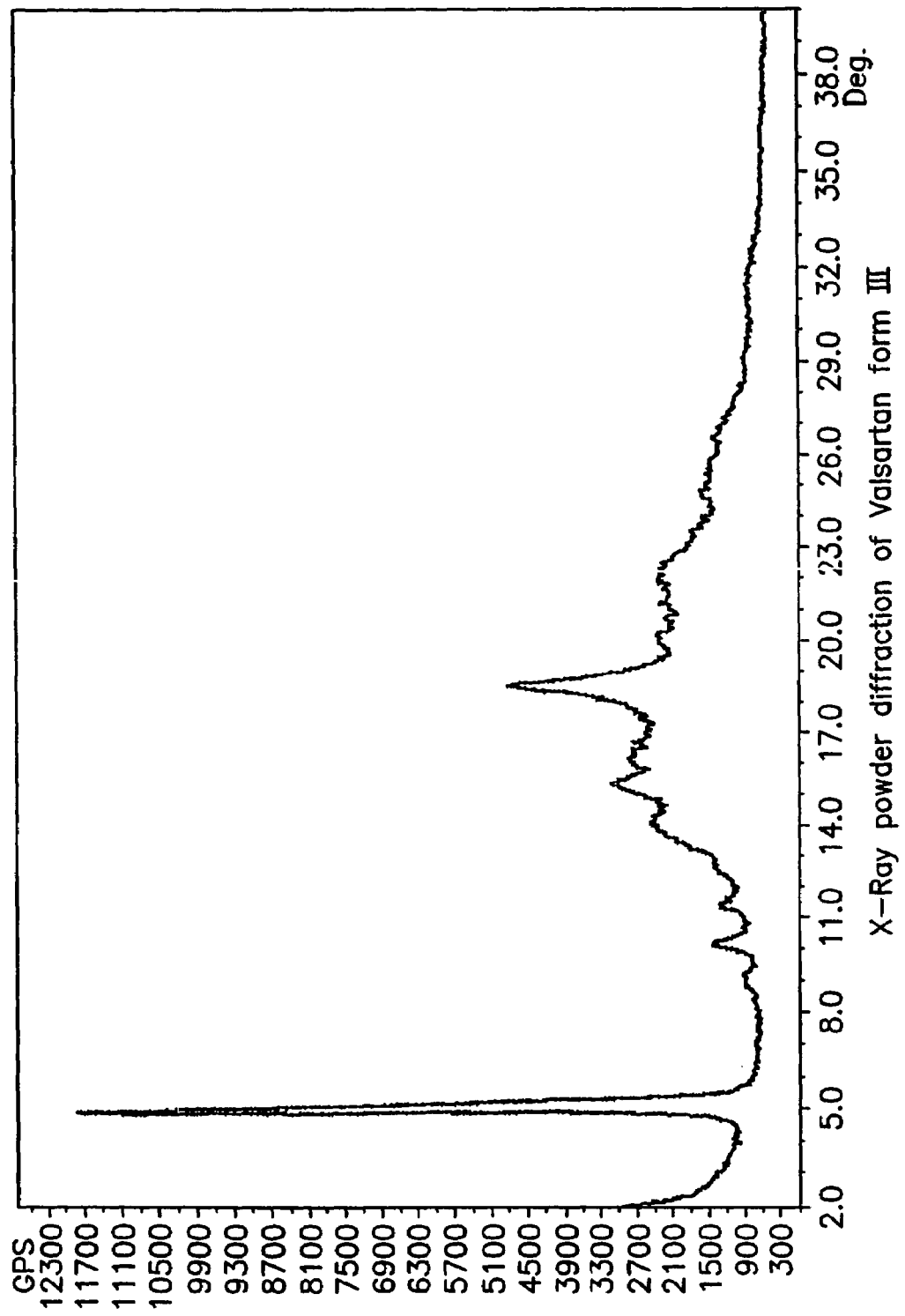
FIG. 6 is an X-Ray powder diffraction of valsartan Form III.
Figure 7:
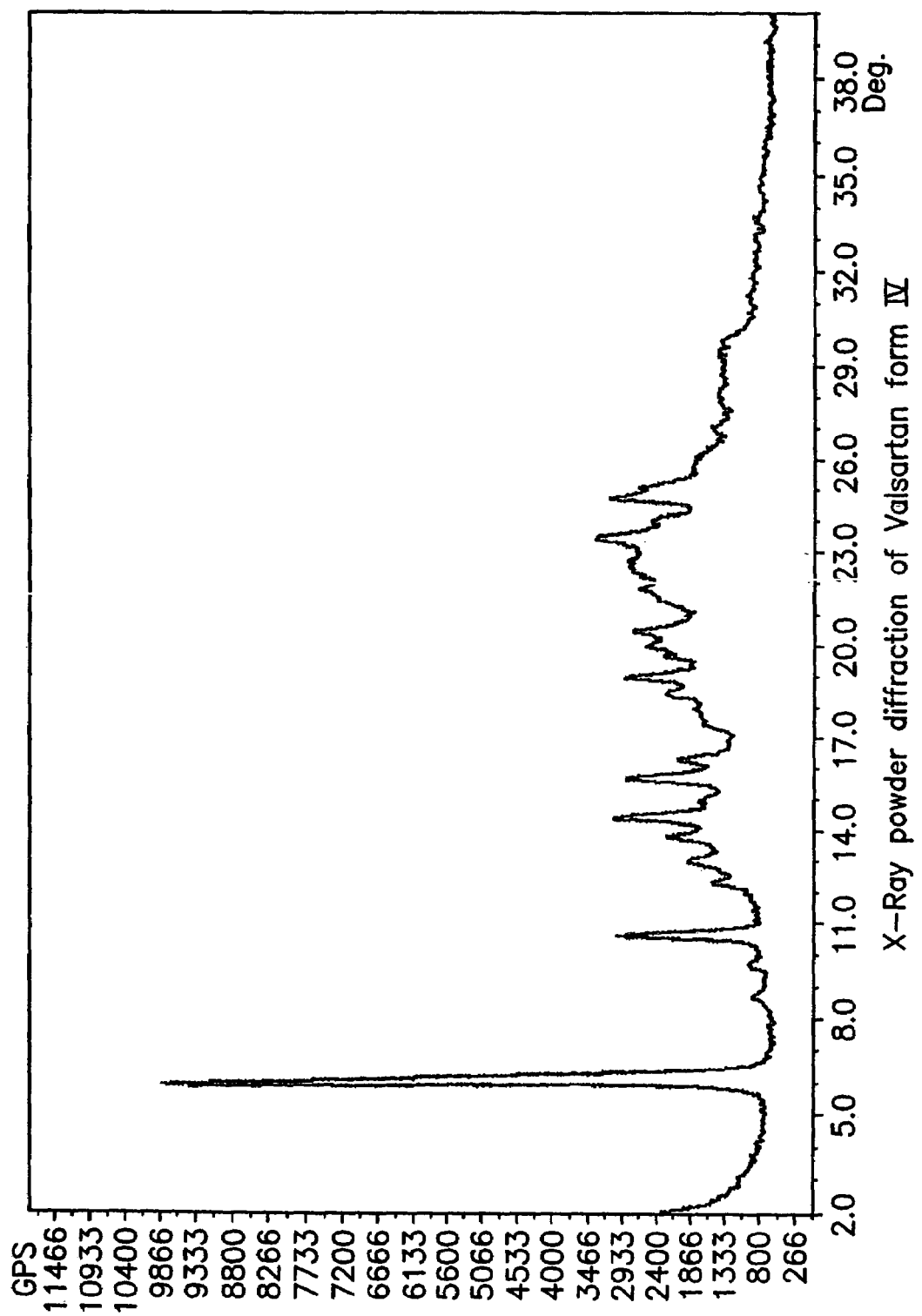
FIG. 7 is an X-Ray powder diffraction of valsartan Form IV.
Figure 8:
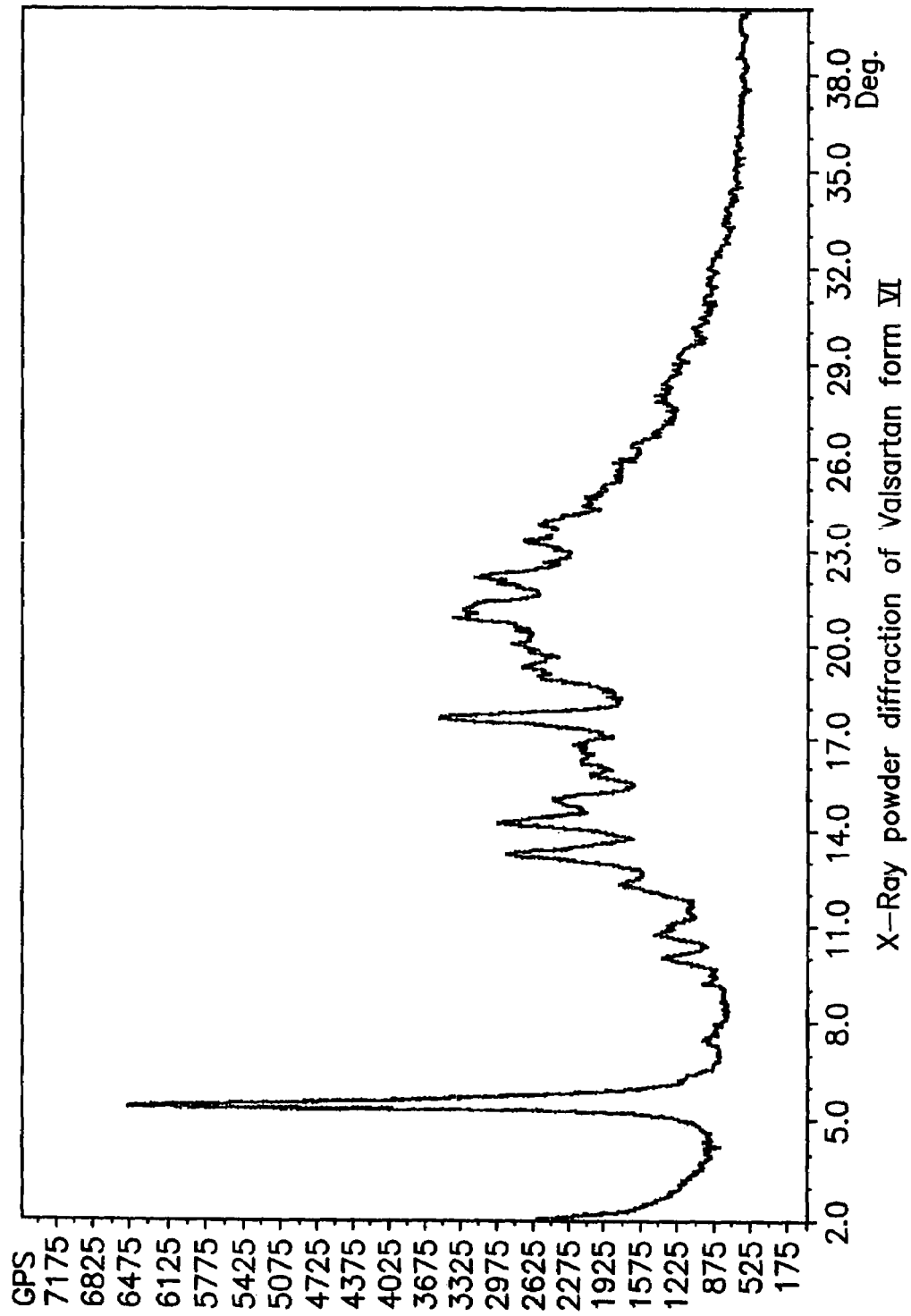
FIG. 8 is an X-Ray powder diffraction of valsartan Form VI.
Figure 9:
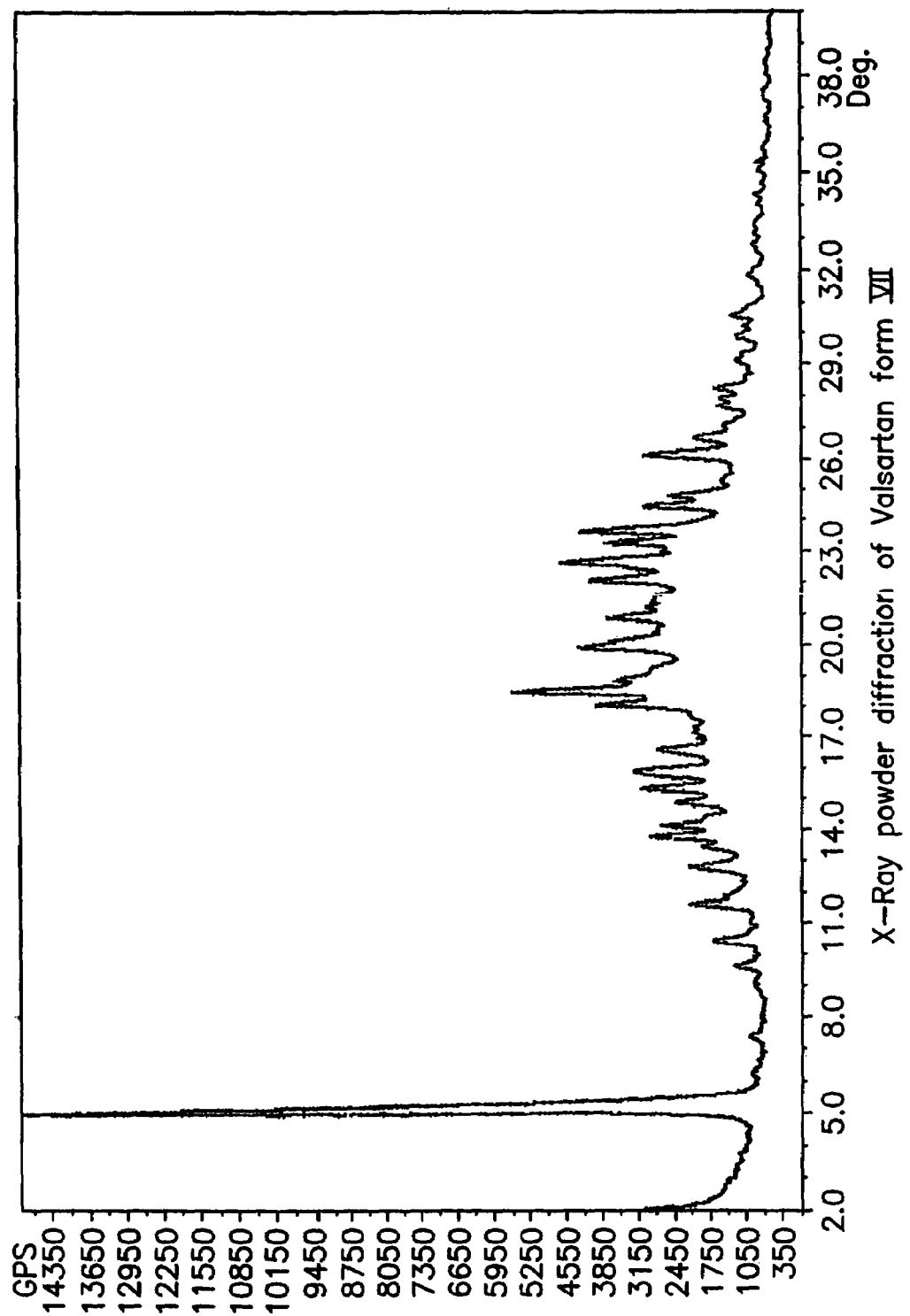
FIG. 9 is an X-Ray powder diffraction of valsartan Form VII.
Figure 10:
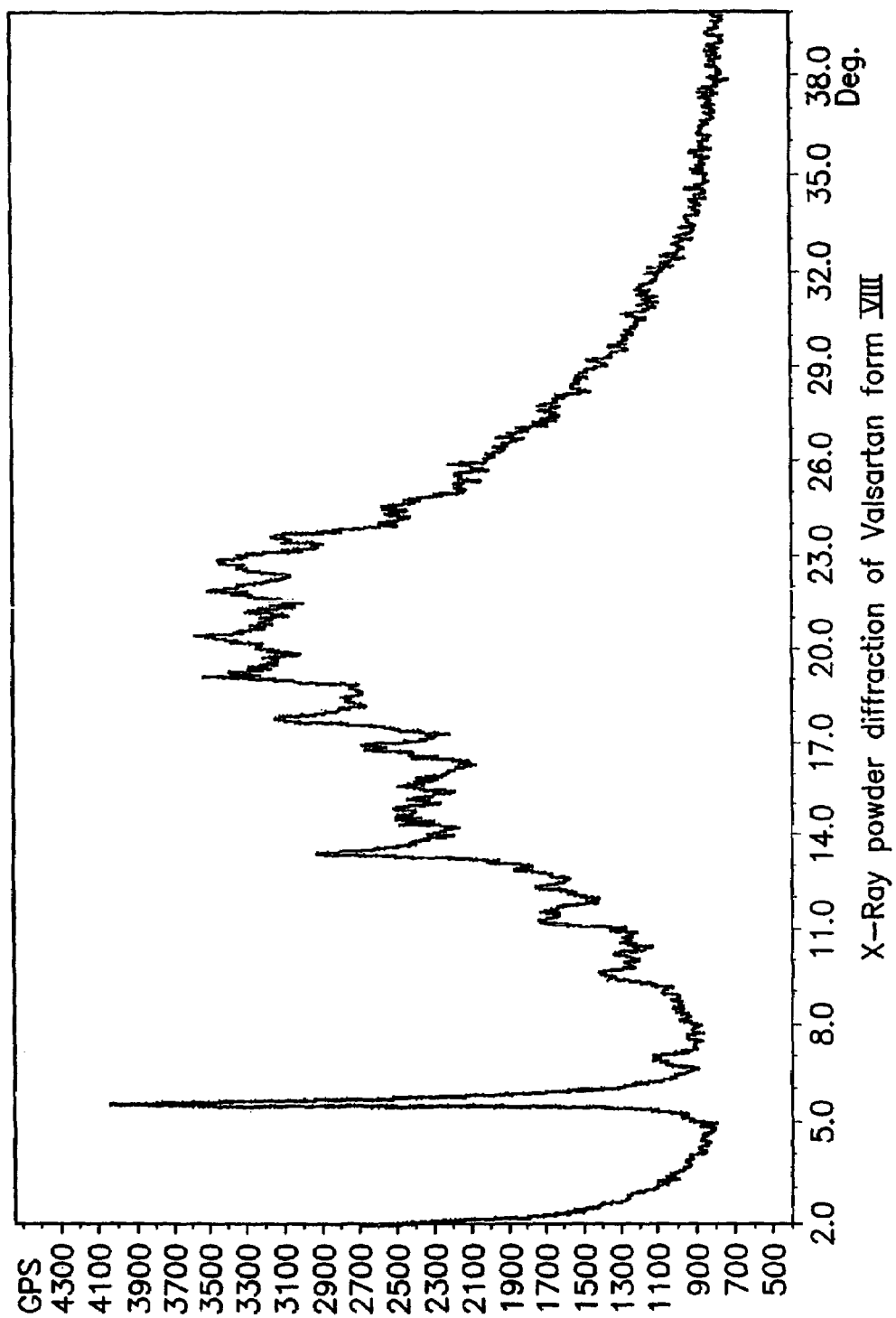
FIG. 10 is an X-Ray powder diffraction of valsartan Form VIII.
Figure 11:
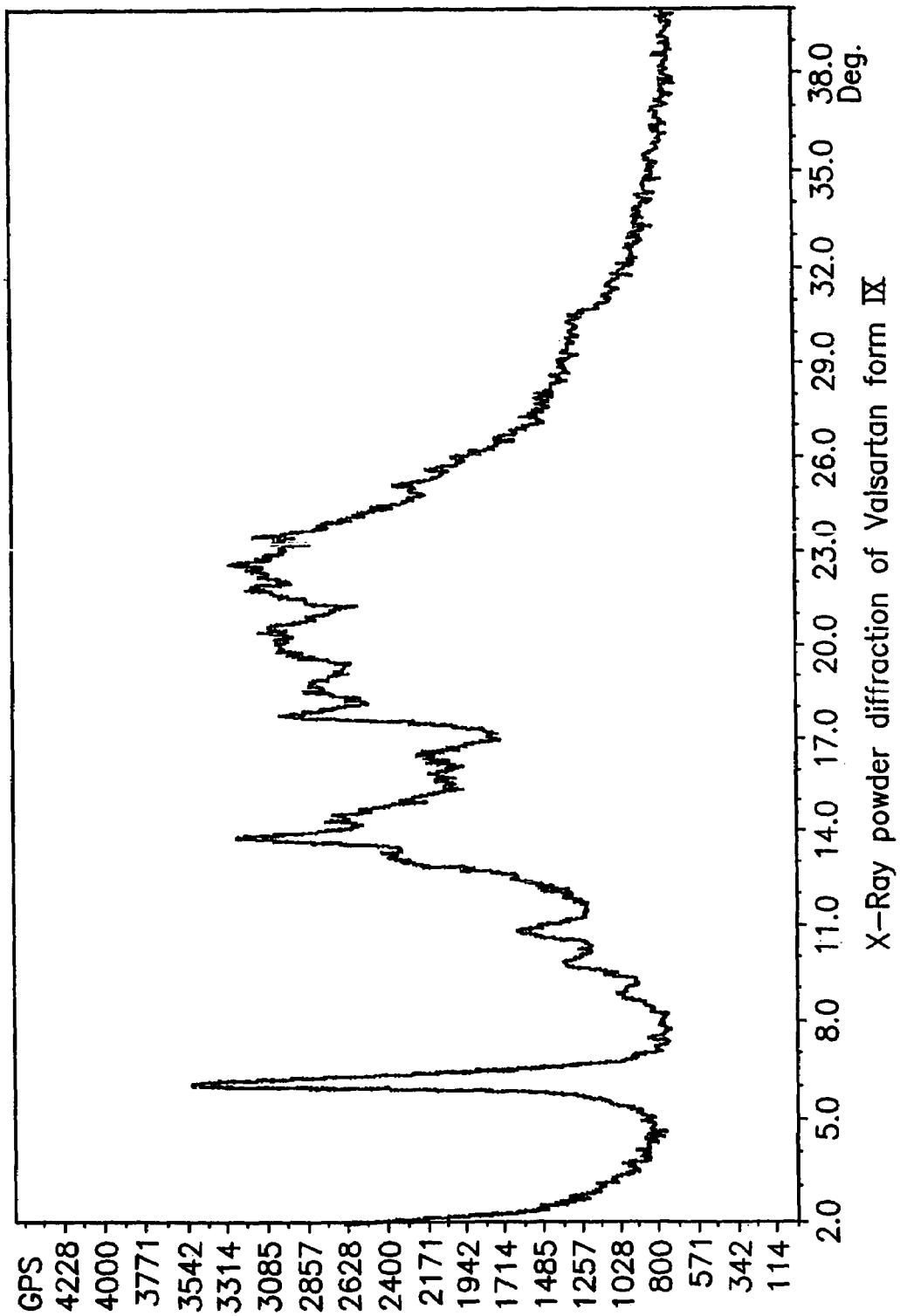
FIG. 11 is an X-Ray powder diffraction of valsartan Form IX.
Figure 12:
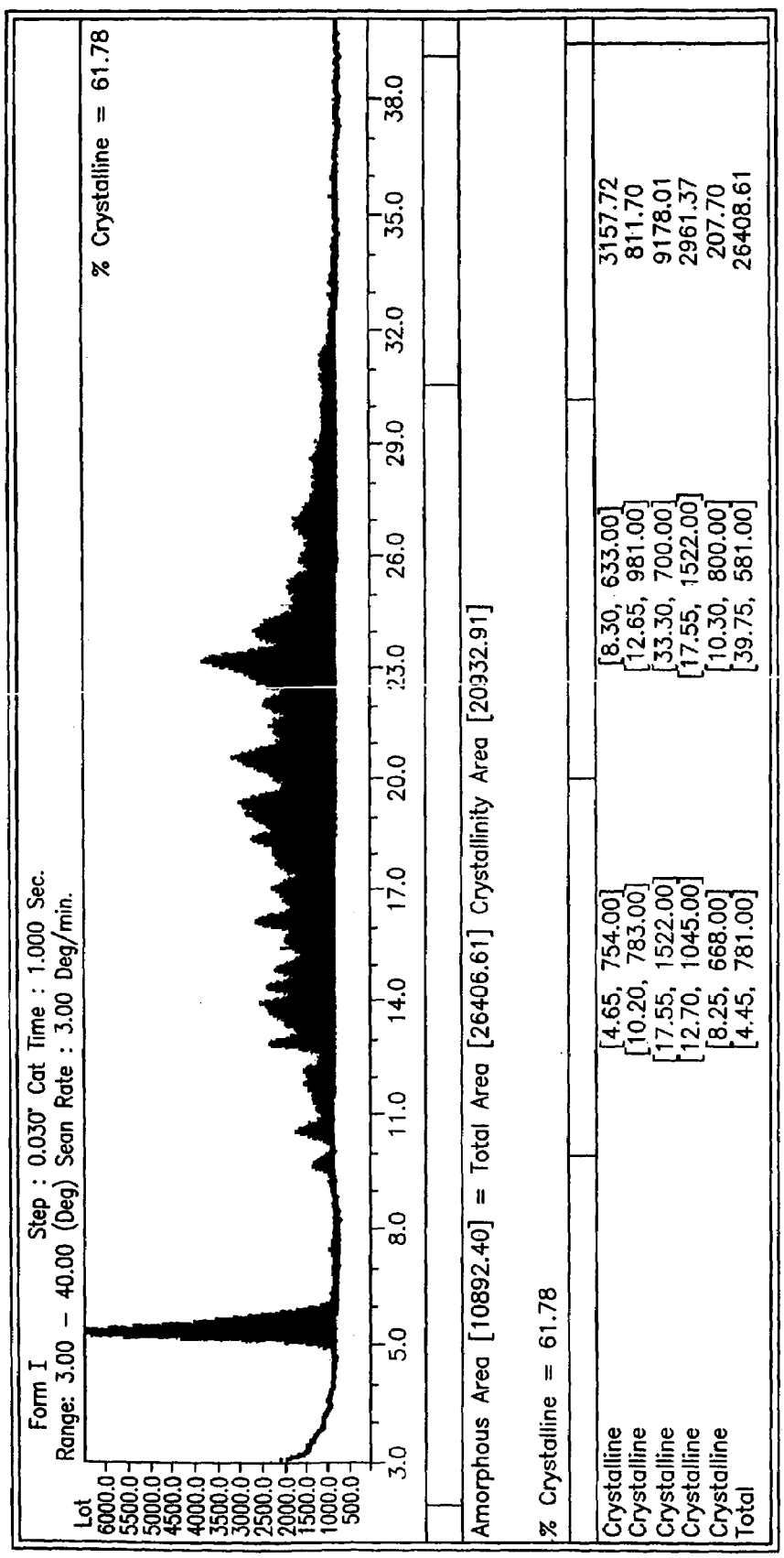
FIG. 12 is a calculation of crystallinity of Form I as an area percentage.
Figure 13:
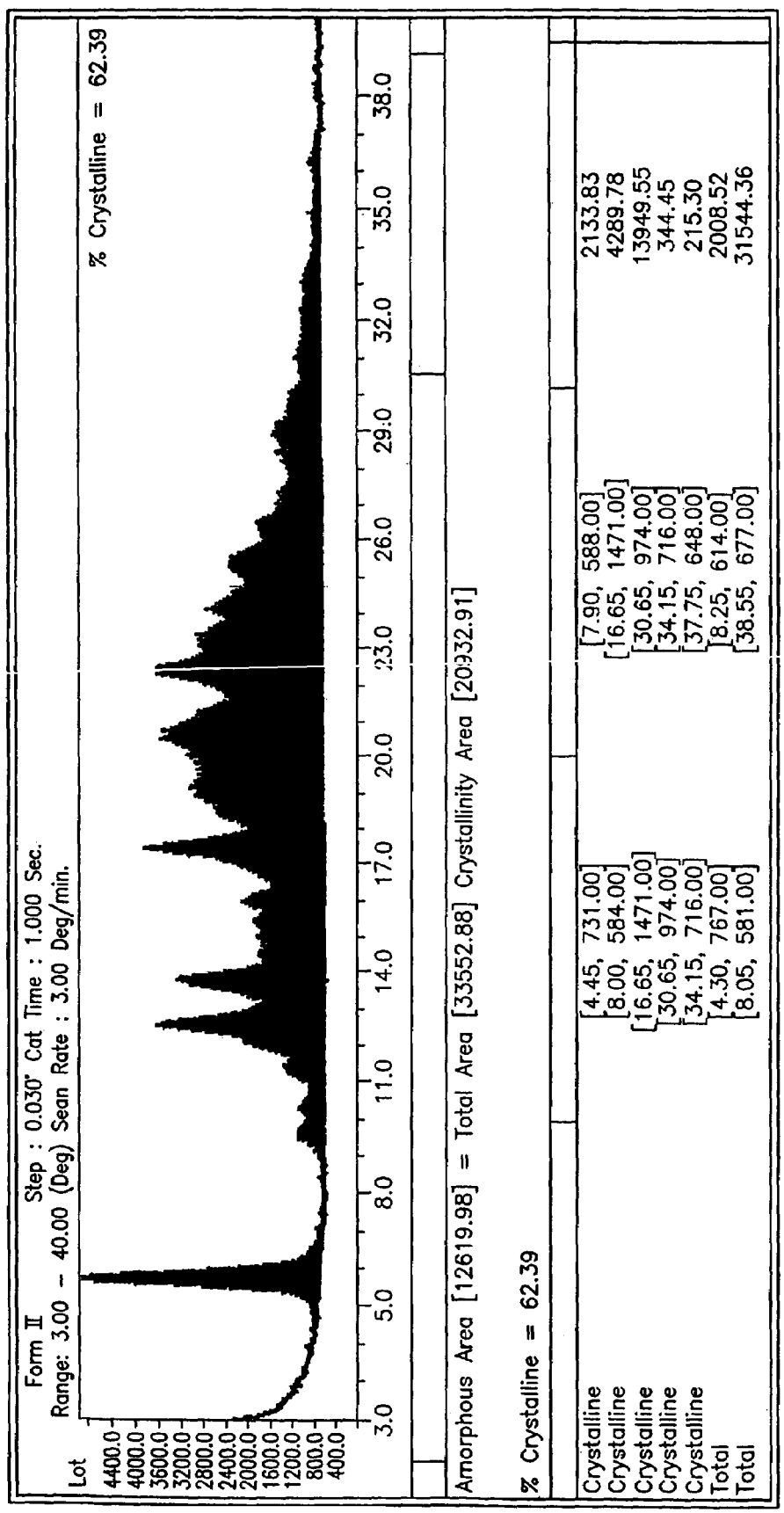
FIG. 13 is a calculation of crystallinity of Form II as an area percentage.
Figure 14:
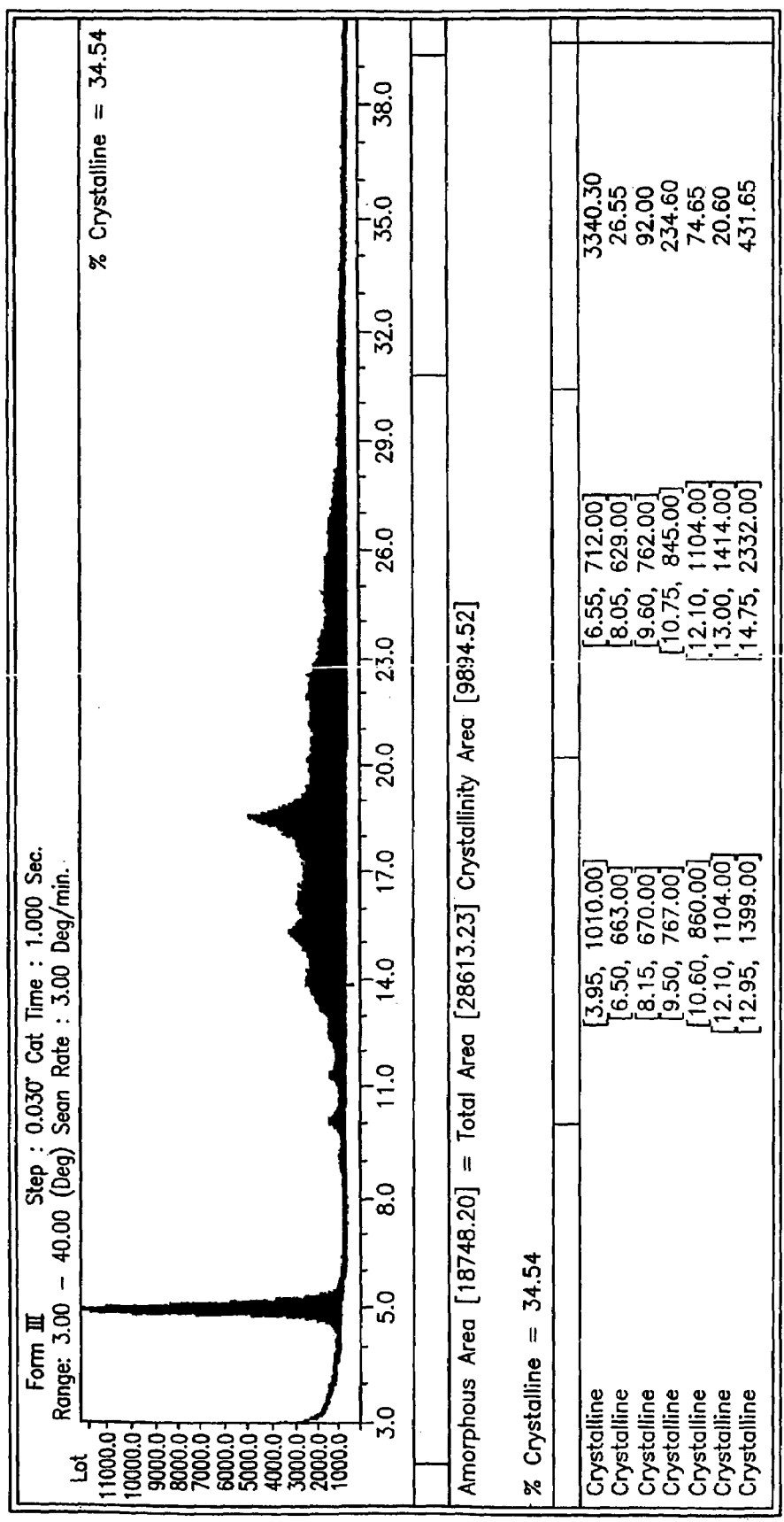
FIG. 14 is a calculation of crystallinity of Form III as an area percentage.
Figure 15:
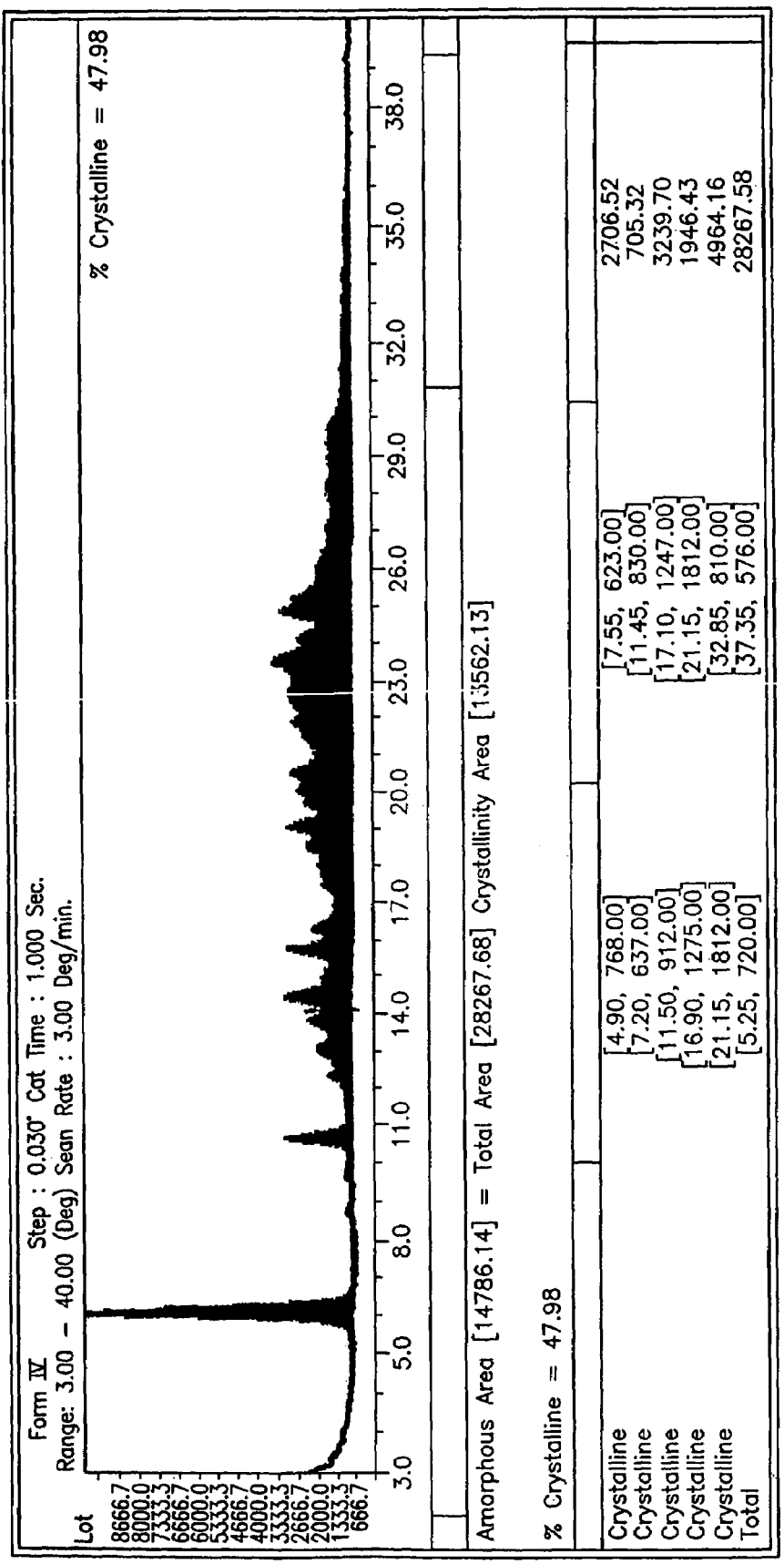
FIG. 15 is a calculation of crystallinity of Form IV as an area percentage.
Figure 16:
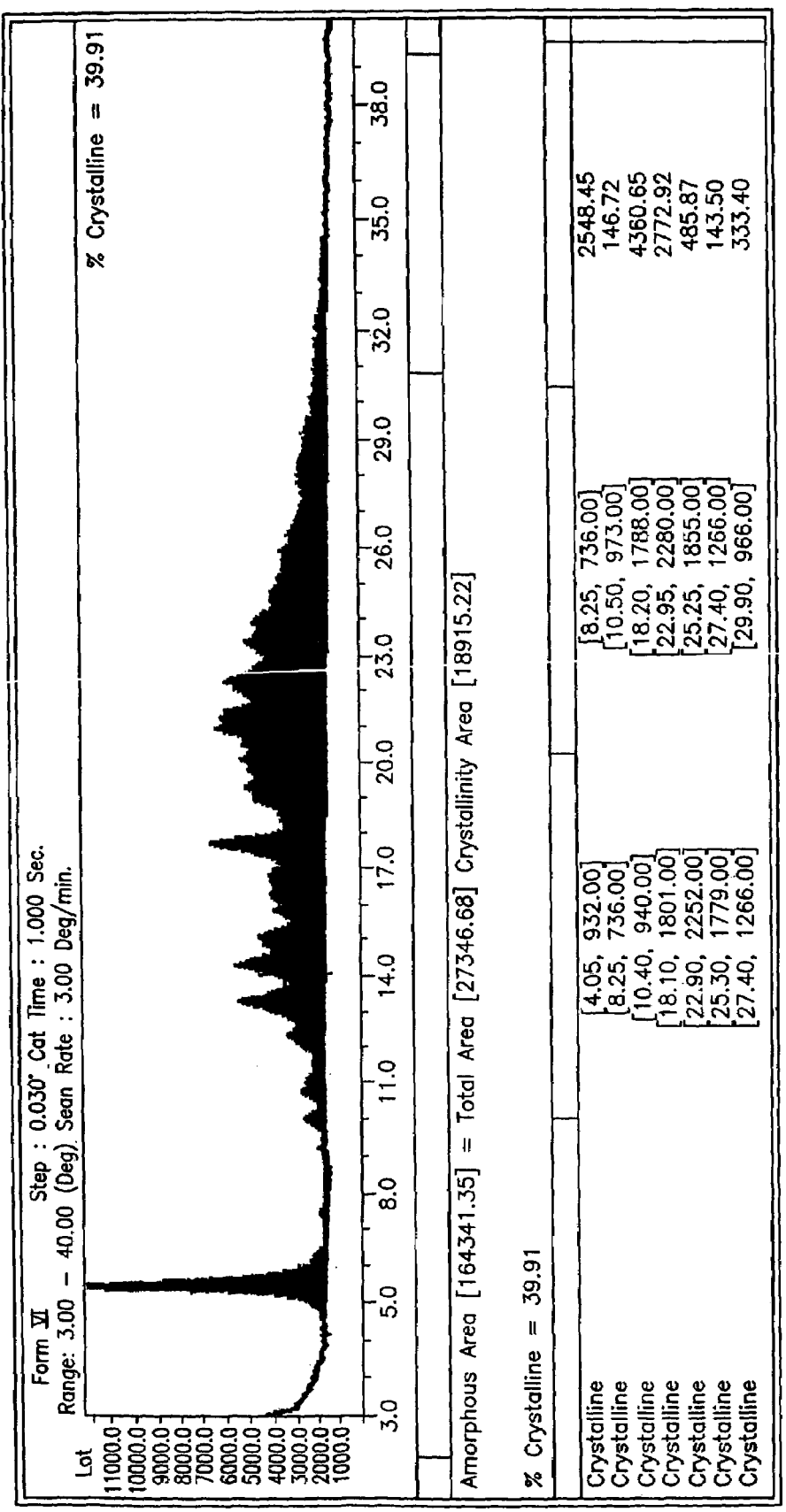
FIG. 16 is a calculation of crystallinity of Form VI as an area percentage.
Figure 17:
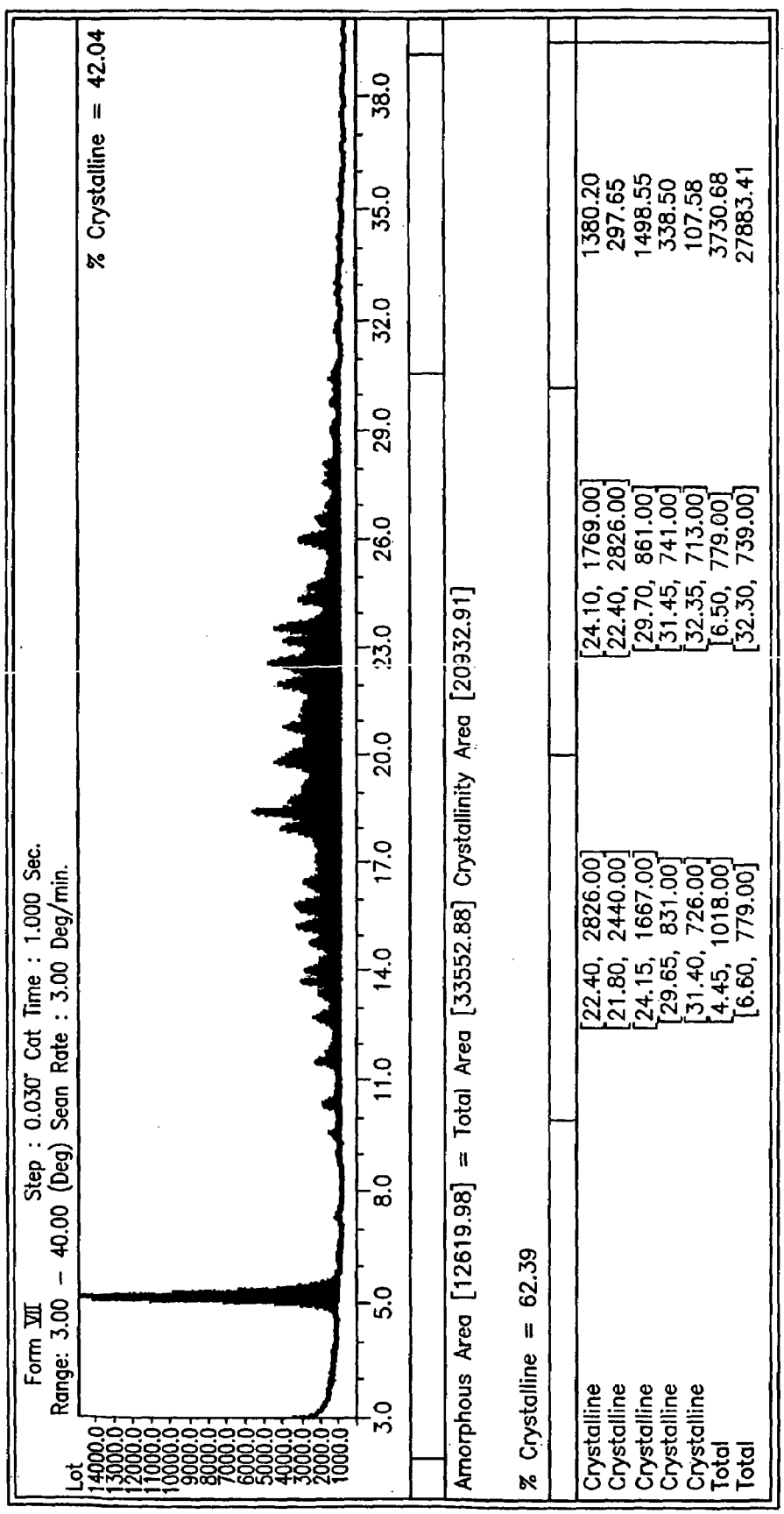
FIG. 17 is a calculation of crystallinity of Form VII as an area percentage.
Figure 18:
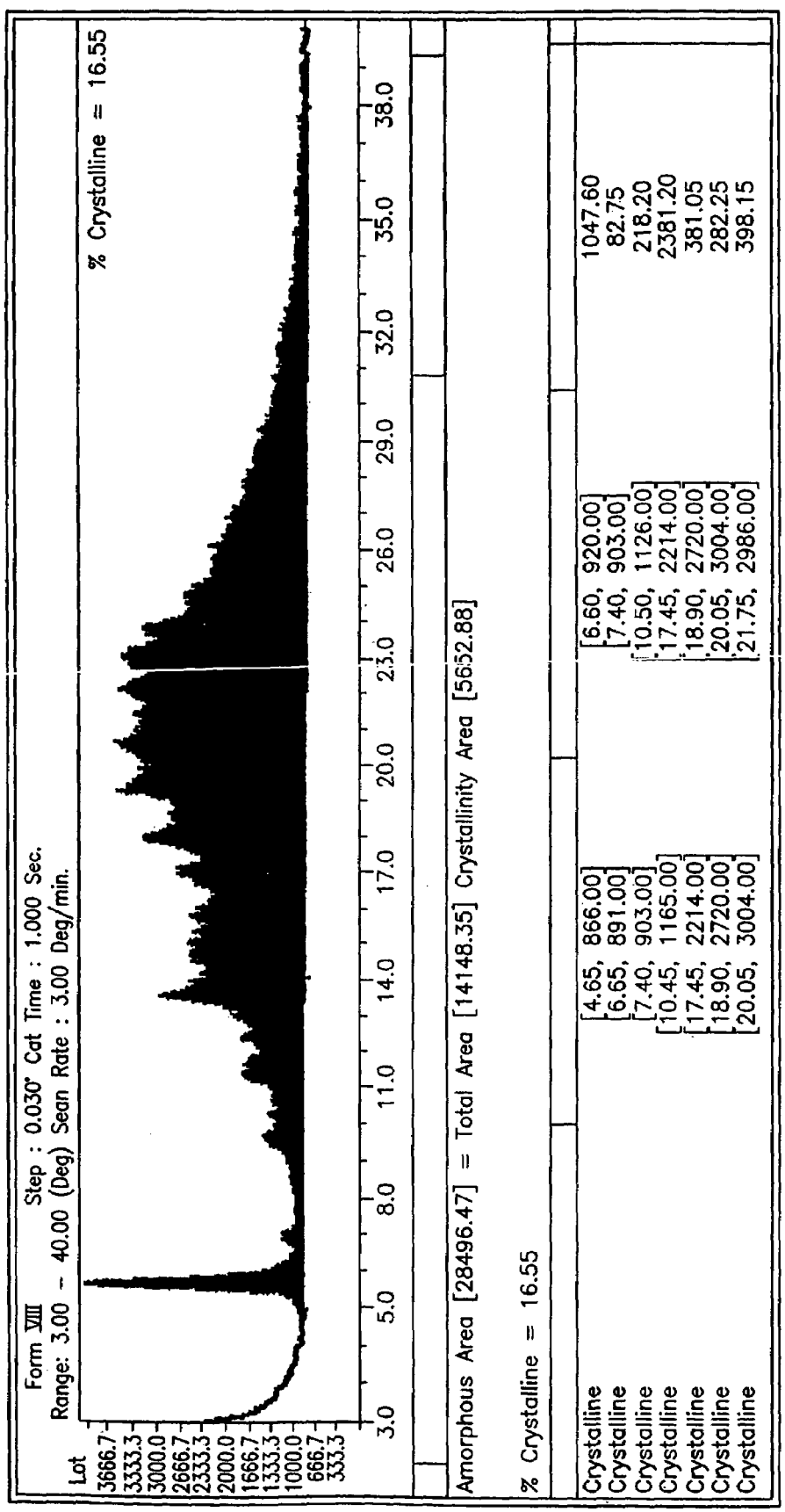
FIG. 18 is a calculation of crystallinity of Form VIII as an area percentage.
Figure 19:
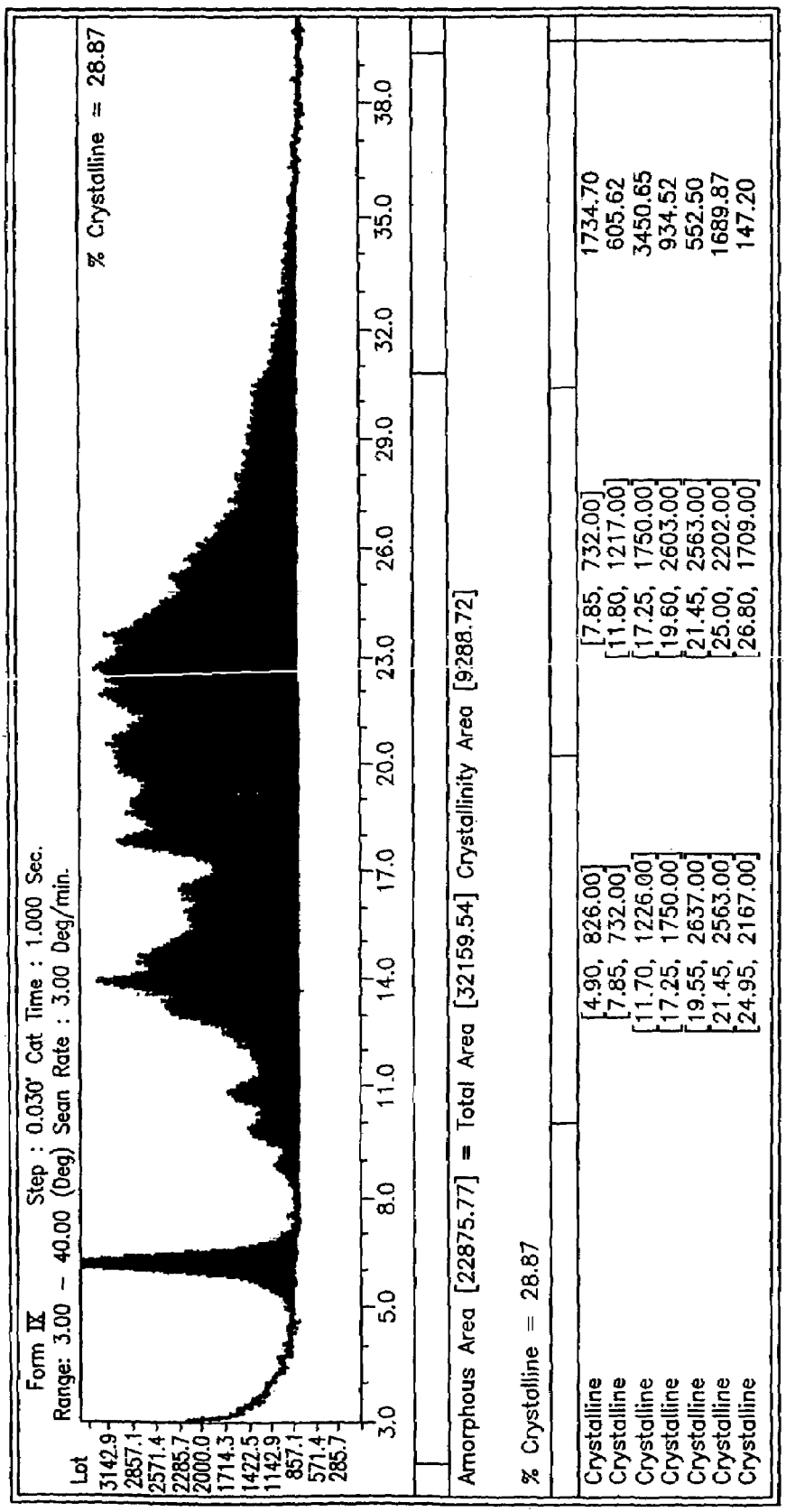
FIG. 19 is a calculation of crystallinity of Form IX as an area percentage.

The amorphous material that is substantially free of crystalline forms is hereby referred to as "valsartan purely amorphous." FIG. 2 illustrates an XRPD pattern for this form, where the halo shape of the pattern illustrates the substantial absence of crystalline structure. Peaks and bumps are particularly missing in the regions characteristic of crystalline form. Additionally, the "valsartan purely amorphous." has a DSC thermogram as substantially depicted in FIG. 3. The DSC thermogram lacks endothermic peaks, such as those above about 1 J/g, preferably those above about 0.5 J/g, in the region of from about 80° C. to about 100° C.

The examples further illustrate processes for obtaining both "valsartan essentially amorphous" and "valsartan purely amorphous."

Many processes of the present invention involve crystallization out of a particular solvent. One skilled in the art would appreciate that the conditions concerning crystallization can be modified without affecting the form of the polymorph obtained. For example, when mixing valsartan in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization.

The conditions may also be changed to induce precipitation. A preferred way of inducing precipitation is to reduce the solubility of the solvent. The solubility of the solvent may be reduced, for example, by cooling the solvent.

In one embodiment, an anti-solvent is added to a solution to decrease its solubility for a particular compound, thus resulting in precipitation. Another way of accelerating crystallization is by seeding with a crystal of the product or scratching the inner surface of the crystallization vessel with a glass rod. Other times, crystallization may occur spontaneously without any inducement. The present invention encompasses both embodiments where crystallization of a particular form of valsartan occurs spontaneously or is induced/accelerated, unless if such inducement is critical.

The starting material used for the processes of the present invention may be any crystalline or amorphous form of valsartan, including any solvates and hydrates. With processes where valsartan goes into solution, the form of the starting material is of minimal relevance since any solid state structure is lost in solution. With suspension and drying processes, the starting material may sometimes make a difference, as one of skill in the art would appreciate.

Pharmaceutical formulations of the present invention contain crystalline valsartan, such as one of those disclosed herein, or valsartan purely amorphous, optionally in mixture with other form(s) of valsartan. The valsartan prepared by the processes of the present invention are ideal for pharmaceutical formulation. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may finction as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, valsartan and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

The active ingredient and excipients may be formulated into compositions and dosage forms according to methods known in the art. The solid oral dosage forms disclosed in U.S. Pat. Nos. 6,485,745 and 6,395,728 may be used as a guidance. The dosages and formulation of DIOVAN may also be used for guidance. The dosage is preferably from about 10 mg to about 1280 mg, more preferably from about 20 mg to about 640 mg, and most preferably from about 40 mg to about 320 mg.

The active pharmaceutical ingredient for the pharmaceutical composition of the present invention is preferably prepared by obtaining a solid from ethyl acetate followed by drying to obtain amorphous form. The solid is preferably obtained by heating valsartan in ethyl acetate to obtain a solution, seeding the solution, preferably with valsartan Form I, and cooling the solution to a temperature of about negative 20° C. to about 20° C. After recovery of the solid for example by filtration, the solid is dried to obtain amorphous form.

The wet solid may be dried for example by heating in a vacuum oven, preferably at a temperature of about 40° C. to about 50° C., under a pressure of less than about 100 mmHg. The process may be stopped when reaching an LOD of 2%. It is also possible to further treat the solid after drying with a fluidized nitrogen atmosphere, particularly when having a higher LOD, such as about 6%, or with a fluidized bed under various conditions.

Instruments

X-Ray powder diffraction data were obtained using by method known in the art using a SCINTAG powder X-Ray diffractometer model X'TRA equipped with a solid state detector. Copper radiation of 1.5418 Å was used. A round aluminum sample holder with round zero background quartz plate, with cavity of 25(diameter)*0.5(dept) mm. DSC analysis was done using a Mettler 821 Stare. The weight of the samples is about 5 mg., the samples were scanned at a rate of 10° C./min from 30° C. to 200° C. The oven was constantly purged with nitrogen gas at a flow rate of 40 ml/min. Standard 40 ml aluminum crucibles covered by lids with three holes were used.

EXAMPLES

Valsartan Purely Amorphous

Example 1

From t-Butyl Acetate 2 g of valsartan was dissolved in 15 mL of refluxed t-BuOAc, resulting in a solution, The solution was allowed to cool to room temperature with slow stirring, cooled to 0° C. and allowed to stand for 2 h. The precipitate was filtered and kept 10 minutes on the filter. X-Ray analysis showed that this sample had crystallized as FORM III. The sample was dried at 50° C./10 mmHg for 2 hours, and an X-Ray analysis showed that the dried sample was purely amorphous, and no endothermic peak was detected in the DSC.

Example 2

From Methyl t-Butyl Ether 5 g of valsartan was dissolved in 20 mL of refluxed MTBE, the resulted solution was allowed to cool to room temperature with slow stirring, then cooled to 0° C. and allow to stand for 3 h. The precipitate was filtered, kept 10 min on the filter and dried at 50° C./10 mmHg for 2 hours. X-Ray analysis showed that this sample was purely amorphous, and no endothermic peak was detected in the DSC.

Example 3

From Diisopropyl Ether 2 g of valsartan in 35 mL of i-$Pr_2$O was refluxed for 1 h and the most of valsartan formed sticky gum residue. The solvent was decanted and the residue was dried at 50° C./10 mmHg for 2 h. X-Ray analysis showed that this sample is purely amorphous, and no endothermic peak was detected in the DSC.

Example 4

From Ethanol-Water Mixture 2 g of valsartan was dissolved in 10 mL of EtOH and 20 mL of $H_2O$ was slowly added with vigorous stirring. The mixture was cooled to 0° C. and allow to stand until complete precipitation of valsartan as a white sticky mass. The solvent was decanted and the residue was dried at 60° C./10 mmHg for 3 hours. X-Ray analysis showed that this sample was purely amorphous, and no endothermic peak was detected in the DSC.

Example 5

From Dimethylformamide-Water Mixture 2 g of valsartan was dissolved in 10 mL of DMF and 20 mL of $H_2O$ was slowly added with vigorous stirring. The mixture was cooled to 0° C. and allowed to stand until all valsartan precipitated as white sticky mass. The solvent was decanted and the residue was dried at 60° C./10 mmHg for 6 h. X-Ray analysis showed that this sample was purely amorphous, and no endothermic peak was detected in the DSC.

Example 6

From Acetone-Water Mixture 2 g of valsartan was dissolved in 10 mL of acetone and 20 mL of $H_2O$ was slowly added with vigorous stirring. The mixture was cooled to 0° C. and allowed to stand until all valsartan precipitated as white sticky mass. The solvent was decanted and the residue was dried at 60° C./10 mmHg for 3 hours. X-Ray analysis showed that this sample was purely amorphous, and no endothermic peak was detected in the DSC.

Example 7

From Water 2 g of valsartan was suspended in 20 mL of $H_2O$ and stirred at 45° C. for 1 hour. The resulted suspension was allowed to cool to room temperature with slow stirring, then cooled to 0° C. and allowed to stand for 2 hours. The precipitate was filtered and kept 10 minutes on the filter. X-Ray analysis showed that the dried sample was purely amorphous.

Example 8

From Tetrahydrofuran 5 g of valsartan was dissolved in 5 mL of refluxed THF. No crystallization was observed under cooling. The solvent was removed under reduced pressure and the sample was dried at 50° C./10 mm Hg for 2 hours. X-Ray analysis showed that this sample was purely amorphous. The DSC thermogram of the sample did not show an endothermic peak.

Example 9

From Dioxane 5 g of valsartan was dissolved in 5 mL of Dioxane with heating. No crystallization was observed under cooling. The solvent was removed under reduced pressure and the sample was dried at 50° C./10 mm Hg for 4 h. X-Ray analysis showed that this sample is purely amorphous. The DSC thermogram of the sample did not show an endothermic peak.

Example 10

From Ethanol 5 g of valsartan was dissolved in 5 mL of EtOH with heating. No crystallization was observed under cooling. The solvent was removed under reduced pressure and the sample was dried at 50° C./10 mm Hg for 3 h. X-Ray analysis showed that this sample was purely amorphous. The DSC thermogram of the sample did not show an endothermic peak.

Example 11

From Isopropanol 5 g of valsartan was dissolved in 5 mL of i-PrOH with heating. No crystallization was observed under cooling. The solvent was removed under reduced pressure and the sample was dried at 50° C./10 mm Hg for 2 hours. X-Ray analysis showed that this sample was purely amorphous.

Example 12

From Diethylether 3 g of valsartan was dissolved in 5 mL of $Et_2O$; the solvent was evaporated under reduced pressure and the sample was dried at 50° C./10 mm Hg for 2 h. This sample also showed by X-Ray to be amorphous.

Example 13

From Acid/Base in Water 3 g of valsartan was dissolved in a solution of NaOH in water (pH~12), and the resulting solution was acidified with 3N aqueous HCl to pH 2. The precipitate was collected by suction filtration, press and kept for 20 minutes. X-Ray analysis showed that this sample was amorphous. The sample was dried at 50° C./10 mmHg for 4 hours; this sample also showed by X-Ray to be amorphous.

Valsartan Essentially Amorphous

Example 14

From Methanol 5 g of valsartan was dissolved in 5 mL of MeOH with heating. No crystallization was observed under cooling. The solvent was removed under reduced pressure and the sample was dried at 50° C./10 mm Hg for 2 hours. X-Ray analysis showed that this sample was essentially amorphous, and in the DSC an endothermic peak at about 80° C. of about 2 J/g was seen.

Example 15

From Heptane 2 g of valsartan was suspended in 20 mL of heptane and stirred at 70° C. for 1 h. The resulting suspension was allowed to cool to room temperature with slow stirring, then cooled to 0° C. and allow to stand for 2 h. The precipitate was filtered and kept 10 minutes on the filter. X-Ray analysis showed that this sample was essentially amorphous. The sample was dried at 50° C./10 mmHg for 2 h. X-Ray analysis showed that the dried sample was essentially amorphous, and in the DSC, an endothermic peak at about 100° C. of about 3 J/g was seen.

Example 16

From Cyclohexane 2 g of valsartan was suspended in 20 mL of cyclohexane and stirred at 70° C. for 1 hour. The resulting suspension was allowed to cool to room temperature with slow stirring, then cooled to 0° C. and allowed to stand for 2 hours. The precipitate was filtered and kept 10 minutes on the filter. X-Ray analysis showed that this sample was essentially amorphous. The sample was dried at 50° C./10 mmHg for 2 hours. X-Ray analysis showed that the dried sample was essentially amorphous, and in the DSC an endothermic peak at about 100° C. of about 12 J/g was seen.

Example 17

From Ethyl Acetate 2 g of valsartan was dissolved in 15 mL of refluxed EtOAc and the resulting solution was allowed to cool to room temperature with slow stirring, then cooled to 0° C. and allowed to stand for 2 hours. The precipitate was filtered and kept 10 min on the filter. X-Ray analysis showed that the sample had crystallized in FORM 1. The sample was dried at 50° C./10 mmHg for 2 hours. X-Ray analysis showed that the dried sample was essentially amorphous and in the DSC an endothermic peak at about 100° C. of about 10 J/g was seen.

Example 18

From Acetone 5 g of valsartan was dissolved in 5 mL of refluxed acetone. The resulting solution was allowed to cool to room temperature with slow stirring, then cooled to 0° C. and allowed to stand for 2 hours. The precipitate was filtered, kept 10 minutes on the filter and dried at 50° C./10 mmHg for 2 hours. X-Ray analysis showed that this sample was essentially amorphous, and in the DSC, an endothermic peak at about 80° C. of about 3 J/g was seen.

Example 19

From n-Butyl Acetate 5 g of valsartan was dissolved in 20 mL of refluxed n-BuOAc, the resulted solution was allowed to cool to room temperature with slow stirring, then cooled to 0° C. and allow to stand for 3 h. The precipitate was filtered, kept 10 min on the filter. X-Ray analysis showed that this sample is crystallized in Form VII. The sample was dried at 50° C./10 mmHg for 2 hours and an X-Ray analysis showed that the dried sample was essentially amorphous, and in the DSC, an endothermic peak at about 90° C. of about 9 J/g was seen.

Valsartan Form II:

Example 20

From Toluene 2 g of valsartan was suspended in 20 mL of toluene and heated to reflux. At reflux point, valsartan melted and formed an emulsion with toluene. The resulted emulsion was allowed to cool to room temperature with slow stirring, then cooled to 0° C. and allowed to stand for 2 hours. The glass-like precipitate was filtered and kept 20 minutes on the filter. X-Ray analysis showed that this sample had crystallized in Form II. The sample was dried at 50° C./10 mmHg for 4 h. X-Ray analysis showed that the dried sample crystailized in Form II.

Preparation of Form VI:

Example 21

From 2-Hexanone 5 g of valsartan was dissolved in 20 mL of 2-hexanone at 80° C. The resulting solution was allowed to cool to room temperature with slow stirring, then cooled to 0° C. and allow to stand for 2 hours. The precipitate was filtered and kept 10 minutes on the filter. X-Ray analysis showed that this sample had crystallized in FORM VII. The sample was dried at 50° C./10 mmHg for 4 hours. X-Ray analysis showed that the dried sample had crystallized in Form VI.

Preparation of Form VIII:

Example 22

From Methyl Ethyl Ketone 5 g of valsartan was dissolved in 20 mL of refluxed MEK. The resulting solution was allowed to cool to room temperature with slow stirring, then cooled to 0° C. and allowed to stand for 2 hours. The precipitate was filtered and kept 10 minutes on the filter. X-Ray analysis showed that this sample had crystallized in FORM I. The sample was dried at 50°

C./10 mmHg for 3 hours. X-Ray analysis showed that the dried sample had crystallized in Form VIII.

Preparation of Form IX

Example 23

From Nitromethane 2 g of valsartan was dissolved in 15 mL of MeNO$_2$ at 80° C. The resulting solution was allowed to cool to room temperature with slow stirring, then cooled to 0° C. and allowed to stand for 2 hours. The precipitate was filtered and kept 10 min on the filter. X-Ray analysis showed that this sample was essentially amorphous. The sample was dried at 50° C./10 mmHg for 4 hours. X-Ray analysis showed that the dried sample had crystallized in form IX.

Example 24

From Acetonitrile 5 g of valsartan was dissolved in 5 mL of refluxed MeCN. The resulting solution was allowed to cool to room temperature with slow stirring, then cooled to 0° C. and allowed to stand for 2 hours. The precipitate was filtered and kept 10 minutes on the filter. X-Ray analysis showed that this sample had crystallized in FORM IV. The sample was dried at 50° C./10 mmHg for 3 hours. X-Ray analysis showed that the dried sample had crystallized in Form IX.

Valsartan Form X

Example 26

5 g of Valsartan was dissolved in 20 mL of refluxed n-BuOAc, the resulted solution was allowed to cool to room temperature with slow stirring, then cooled to 0° C. and allow to stand for 3 h. The precipitate was filtered, kept 10 min on the filter and dried at 50° C./10 mmHg for 2 h (dry sample) and Form X was recovered.

Valsartan Form XI

Example 27

1 g of Valsartan (form II) was triturated from 10 ml of Toluene at 50° C. for 0.5 h. The suspension was cooled to 0–4° C., filtered and dried at 50° C./10 mmHg for 2 h and Form XI was recovered.

Example 28

1 g of Valsartan (form VII) was placed for two weeks at room temperature in Toluene vapor atmosphere and Form XI was recovered.

Valsartan Essentially Amorphous

Example 29

1 g of Valsartan (form V) was placed for two weeks at room temperature in Hexane vapor atmosphere and valsartan essentially amorphous was recovered.

Example 30

1 g of Valsartan (form VI) was placed for two weeks at room temperature in Hexane vapor atmosphere and valsartan essentially amorphous was recovered.

Example 31

1 g of Valsartan (form VII) was placed for two weeks at room temperature in Hexane vapor atmosphere and valsartan essentially amorphous was recovered.

Valsartan Form XIII

Example 32

1 g of Valsartan (form III) was placed for two weeks at room temperature in Water vapor atmosphere and Form XIII was recovered.

Example 33

1 g of Valsartan (form V) was placed for two weeks at room temperature in Water vapor atmosphere and Form XIII was recovered.

Example 34

1 g of Valsartan (form VI) was placed for two weeks at room temperature in Water vapor atmosphere and Form XIII was recovered.

Example 35

1 g of Valsartan (form VII) was placed for two weeks at room temperature in Water vapor atmosphere and Form XIII was recovered.

Example 36

1 g of Valsartan (form VIII) was placed for two weeks at room temperature in Water vapor atmosphere and Form XIII was recovered.

Example 37

1 g of Valsartan (form IX) was placed for two weeks at room temperature in Water vapor atmosphere and Form XIII was recovered.

Example 38

1 g of Valsartan (Amorphous) was placed for two weeks at room temperature in Water vapor atmosphere and Form XIII was recovered.

Preparation of Wet, Crude and Dry Valsartan

Example 39

Preparation of Wet Valsartan

A 100 liters reactor equipped with mechanical stirrer, condenser and thermometer, was charged with valsartan crude wet (9.7 Kg) and EtOAc (46.3 L). The jacket was then heated to 50° C. and stirred at a rate of 95 rpm until getting a clear solution. The stirring at this temperature was continued for 1 hour. Then the clear solution was cooled to 33–38° C. and seeded with 5.1 g of VLS in order to crystallize Valsartan. At the end of the addition the stirring was maintained for about 1 hour at 34–36° C., then cooled during 2 hours until 23–25° C. and maintained while stirring for 0.5 hours at this temperature. The slurry was then cooled during 2.5 hours until 0° C. (±5° C.) and maintained while stirring for 0.5 hours at this temperature. The slurry was then filtered and washed with EtOAc (5.1 L) to obtain 8.8 Kg of wet material. This material was analyzed by XRD and found to be crystal form I (see FIG. 23).

Example 39

Drying the Wet Valsartan with Vacuum Dryer While Stirring 600 g of Valsartan prepared according to example 38 were put in the drying apparatus while heating to 45° C. under vacuum (less than 60 mm Hg). The solid was maintained for 2 hours without stirring, and then the stirrer was put on (15–20 rpm) for about 7 hours until the loss on drying reach not more than 2%. The XRD pattern showed that the material is essentially amorphous, and the DSC showed an endotherm with enthalpy 29 J/g Example 40

Drying the Wet Valsartan with Vacuum Dryer While Stirring then Humidification with Humid Nitrogen 600 g of Valsartan prepared according to example 38 were put in the drying apparatus while heating to 45° C. under vacuum (less than 60 mm Hg). The solid was maintained for 2 hours without stirring, and then the stirrer was put on (15–20 rpm) for about 4 hours until the loss on drying reach 6.5%. 60 g of the so obtained solid was put in a 0.5 L reactor at 50° C. under stirring (20 rpm). To this solid was flowed humidified nitrogen during 2 hours. Then the nitrogen was stopped and the solid was put under vacuum (less than 30 mm Hg) for 3 hours. The vacuum was stopped and humidified nitrogen was flowed inside the reactor for 2 hours (humidification of the nitrogen was done by bubbling nitrogen through a vessel of water). Then the nitrogen was stopped again and the solid was put again under vacuum (less than 30 mm Hg) for 5 hours.

The XRD pattern showed that the material is essentially amorphous, and the DSC showed an endotherm with enthalpy 29 J/g Example 41

Drying the Wet Valsartan with Vacuum Dryer While Stirring then Humidification with Fluidized Bed.

85 g of the material obtained in example 39 (after drying with stirring and LOD=2%) was put in the fluidized bed at 30–40° C. during 13 hours. The XRD pattern showed that the material is essentially amorphous, and the DSC showed an endotherm with enthalpy 29 J/g.

Example 42

Preparation of Crude Valsartan

A 460 liters reactor equipped with mechanical stirrer, condenser and thermometer, was charged at ambient temperature under stirring with Trityl valsartan (30 Kg ), Acetone (120 L), water (31 L) and an aqueous mixture of $H_2SO_4$ 66% (8.4 Kg). The suspension was then heated to 35° C.–40° C. and stirred at a rate of 80–100 rpm for about 6 hours until the end of the reaction (monitoring by TLC). To the solution was added water (38 L) and the solution was then cooled to 22±5° C. and basified with an aqueous mixture of NaOH 47% (14.4 Kg) while maintaining the temperature below 35° C. At the end of the addition, the temperature was 30° C. and the pH was 12–13. The reactor jacket was then heated to 45° C. and the acetone of the reaction mixture was distilling off under vacuum (less than 150 mm Hg). At the end of the distillation the jacket was cooled to 30° C., water (30 L) and EtOAc (66 L) were added. The 2 phases were stirred for 30 minutes, and the stirring was stopped for about 25 minutes. The phases were separated.

The aqueous phase so obtained was returned to the reactor and EtOAc (33 L) was added and stirred for 30 minutes, then the stirring was stopped for 30 minutes and the separation of the two phases was performed. The aqueous phase was returned to the reactor and was acidified with an aqueous mixture of $H_2SO_4$ 66% (8.4 Kg) until reaching a pH between 2 to 3 while maintaining the temperature below 30° C. EtOAc (150 L) was then added and stirred for 30 minutes, then the stirring was stopped for 30 minutes, a phase separation was performed and the aqueous phase was discarded. The reactor jacket was then heated to 45° C. and the organic phase was distilled off under vacuum (less than 150 mm Hg). EtOAc (90 L) was then added and distilled off under the same conditions than before.

The distillation leaded to a solid residue in the reactor. Then the vacuum was stopped and EtOAc (110 L) was added while the reactor was heated to 50° C. until getting a almost clear solution. The heating was continued for 1 hour while performing a recycling with filtration. Then the clear solution was cooled to 33–38° C. and seeded with 15 g of Valsartan. At the end of the addition the stirring was maintained for 0.5 hours at 33–38° C., then cooled during 2 hours until 23–25° C. and maintained while stirring for 0.5 hours at this temperature. The slurry was then cooled during 2 hours until 0–2° C. and maintained while stirring for 0.5 hours at this temperature. The suspension was then filtered with centrifuge, washed with EtOAc (15 L) to obtain 30.3 Kg of wet material.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 may be used for guidance. All references mentioned herein are incorporated in their entirety.

Notations of the various polymorphic forms in parenthesis in the claims are for reference purposes only, and are not intended to limit the claim.

What is claimed is:

1. A process for preparing the crystalline valsartan (Form 1) having an XRPD pattern with peaks at 5.4, 13.0, 16.3, 19.5, 20.7, 23.4±0.2 degrees 2-theta comprising the steps of:
   a) heating a solution of valsartan in a solvent selected from the group consisting of methyl ethyl ketone and ethyl acetate;
   b) cooling the solution to a temperature of about negative 20° C. to about 20° C. to induce crystallization; and
   c) recovering the crystalline valsartan without heating.

2. The process of claim 1, wherein the solvent is methyl ethyl ketone.

* * * * *